US012721866B2

(12) United States Patent
O'Heeron et al.

(10) Patent No.: US 12,721,866 B2
(45) Date of Patent: Sep. 1, 2026

(54) THERAPEUTIC USE OF FIBROBLASTS FOR USE IN WOUND HEALING

(71) Applicant: FIBROBIOLOGICS, INC., Houston, TX (US)

(72) Inventors: Pete O'Heeron, Houston, TX (US); Hamid Khoja, Houston, TX (US)

(73) Assignee: Fibrobiologics, Inc., Houston, TX (US)

( * ) Notice: Subject to any disclaimer, the term of this patent is extended or adjusted under 35 U.S.C. 154(b) by 440 days.

(21) Appl. No.: 18/184,726

(22) Filed: Mar. 16, 2023

(65) Prior Publication Data

US 2023/0293595 A1 Sep. 21, 2023

Related U.S. Application Data

(60) Provisional application No. 63/383,498, filed on Nov. 13, 2022, provisional application No. 63/379,220, filed on Oct. 12, 2022, provisional application No. 63/320,388, filed on Mar. 16, 2022.

(51) Int. Cl.

| | |
|---|---|
| ***A61K 35/33*** | (2015.01) |
| ***A61K 9/00*** | (2006.01) |
| ***A61L 26/00*** | (2006.01) |
| ***C12N 5/077*** | (2010.01) |

(52) U.S. Cl.

CPC ............ *A61K 35/33* (2013.01); *A61K 9/0014* (2013.01); *A61L 26/00* (2013.01); *C12N 5/0656* (2013.01); *C12N 2527/00* (2013.01)

(58) Field of Classification Search

CPC .............................. C12N 5/0656; A61K 35/33

See application file for complete search history.

(56) References Cited

U.S. PATENT DOCUMENTS

| | | | | |
|---|---|---|---|---|
| 5,266,480 | A | 11/1993 | Naughton et al. | |
| 5,460,939 | A | 10/1995 | Hansbrough et al. | |
| 9,598,673 | B2 | 3/2017 | Ichim et al. | |
| 12,310,991 | B2 * | 5/2025 | O'Heeron | A61P 9/10 |
| 2007/0184033 | A1 | 8/2007 | Sevrain et al. | |
| 2010/0035815 | A1 | 2/2010 | Li et al. | |
| 2010/0216210 | A1 | 8/2010 | Sevrain et al. | |
| 2010/0285090 | A1 | 11/2010 | Sevrain et al. | |
| 2010/0285091 | A1 | 11/2010 | Sevrain et al. | |
| 2010/0285092 | A1 | 11/2010 | Sevrain et al. | |
| 2010/0285093 | A1 | 11/2010 | Sevrain et al. | |
| 2011/0014164 | A1 | 1/2011 | Huangfu et al. | |
| 2011/0020291 | A1 * | 1/2011 | Banerjee | C12N 5/0663 435/325 |
| 2011/0275151 | A1 | 11/2011 | Sevrain et al. | |
| 2011/0286978 | A1 | 11/2011 | Klimanskaya et al. | |
| 2012/0093885 | A1 | 4/2012 | Sahoo et al. | |
| 2013/0195899 | A1 | 8/2013 | Ichim et al. | |
| 2013/0209528 | A1 | 8/2013 | Levi et al. | |
| 2014/0044682 | A1 | 2/2014 | O'Heeron | |
| 2014/0289882 | A1 | 9/2014 | Zhu et al. | |
| 2014/0314726 | A1 | 10/2014 | O'Heeron et al. | |
| 2014/0377231 | A1 | 12/2014 | O'Heeron | |
| 2015/0023908 | A1 | 1/2015 | Al-Qahtani | |
| 2015/0079046 | A1 | 3/2015 | Sinden et al. | |
| 2016/0145575 | A1 | 5/2016 | Pimanda et al. | |
| 2016/0213764 | A1 | 7/2016 | Wagner et al. | |
| 2016/0220613 | A1 | 8/2016 | Lim | |
| 2016/0220699 | A1 | 8/2016 | O'Heeron | |
| 2016/0243171 | A1 | 8/2016 | Shiels et al. | |
| 2017/0037374 | A1 | 2/2017 | Yamamoto et al. | |
| 2017/0087277 | A1 | 3/2017 | Sevrain et al. | |
| 2018/0055887 | A1 | 3/2018 | Lu et al. | |
| 2018/0195044 | A1 | 7/2018 | O'Heeron et al. | |
| 2018/0236005 | A1 | 8/2018 | O'Heeron et al. | |
| 2018/0318466 | A1 | 11/2018 | Sevrain et al. | |
| 2019/0022145 | A1 | 1/2019 | O'Heeron | |
| 2019/0142871 | A1 | 5/2019 | O'Heeron | |
| 2019/0307794 | A1 | 10/2019 | Hong et al. | |
| 2020/0289583 | A1 | 9/2020 | Ferreira et al. | |
| 2020/0338133 | A1 * | 10/2020 | O'Heeron | A61K 35/33 |
| 2021/0128636 | A1 | 5/2021 | O'Heeron et al. | |
| 2021/0154230 | A1 | 5/2021 | O'Heeron et al. | |
| 2021/0180020 | A1 | 6/2021 | O'Heeron et al. | |
| 2021/0213069 | A1 | 7/2021 | Hu et al. | |
| 2021/0230551 | A1 | 7/2021 | O'Heeron et al. | |

(Continued)

FOREIGN PATENT DOCUMENTS

| | | | | |
|---|---|---|---|---|
| CN | 104011201 | 8/2014 | | |
| EP | 3566713 A1 * | 11/2019 | | A61L 27/20 |

(Continued)

OTHER PUBLICATIONS

PCT International Search Report and Written Opinion issued in International Application No. PCT/US2023/064498, dated Jun. 29, 2023.

Extended European Search Report issued in European Patent Application No. 23162313.3, dated Jul. 5, 2023.

Alt et al., "Fibroblasts share mesenchymal phenotypes with stem cells, but lack their differentiation and colony-forming potential", Bio Cell, 103(4):197-208, 2011.

Anokye-Danso et al., "Highly Efficient miRNA-Mediated Reprogramming of Mouse and Human Somatic Cells to Pluripotency," Cell Stem Cell, 8:376-388, 2011.

Arora, "Cell Culture Media: A Review," Mater. Methods, 3(175):1-29, 2013.

Balducci et al., "The differences between mesenchymal stromal cells and fibroblasts", Chapter 30, The Biology and Therapeutic Application of Mesenchymal Cells: The Cellular and Molecular Biology of Mesenchymal Stromal Cells, John Wiley and Sons, 2017.

(Continued)

*Primary Examiner* — Yong D Pak

(74) *Attorney, Agent, or Firm* — Norton Rose Fulbright US LLP

(57) ABSTRACT

Uses for activated or inactivated fibroblasts or fibroblast-derived materials, such as exosomes from fibroblasts, for wound care are provided. The methods and compositions are useful for purpose of tissue differentiation, cell recruitment, differentiation of local stem cells, and expansion of local cells, such as keratocytes, vasal epithelial cells, myofibroblasts, and/or dermal fibroblasts, including for initiating and/or maintaining wound healing.

19 Claims, 22 Drawing Sheets

(56) References Cited

U.S. PATENT DOCUMENTS

| | | | |
|---|---|---|---|
| 2021/0244769 | A1 | 8/2021 | O'Heeron et al. |
| 2021/0393700 | A1 | 12/2021 | O'Heeron et al. |

FOREIGN PATENT DOCUMENTS

| | | |
|---|---|---|
| JP | 2013/537538 | 10/2013 |
| WO | WO 2000/073418 | 12/2000 |
| WO | WO 2001/014527 | 3/2001 |
| WO | WO 2008/020119 | 2/2008 |
| WO | WO 2009/100029 | 8/2009 |
| WO | WO 2010/088775 | 8/2010 |
| WO | WO 2010/138517 | 12/2010 |
| WO | WO 2011/140323 | 11/2011 |
| WO | WO 2014/170488 | 10/2014 |
| WO | WO 2015/179227 | 11/2015 |
| WO | WO 2016/201323 | 12/2016 |
| WO | WO 2018/062269 | 4/2018 |
| WO | WO 2018/195308 | 10/2018 |
| WO | WO 2019/231562 | 12/2019 |
| WO | 110 975 000 | 4/2020 |
| WO | WO 2021/256751 | 12/2021 |
| WO | WO 2022/047486 | 3/2022 |

OTHER PUBLICATIONS

Cell Guidance System, "Conditioning cell culture media," retrieved from the internet at www.cellgs.com/blog/conditioning-cell-culture-media.html, 5 pages, 2020.

Cheng et al., "Generation of neural progenitor cells by chemical cocktails and hypoxia," Cell Research, 24:665-679, 2014.

Cheng et al., "Mesenchymal stem cells deliver exogenous miR-21 via exosomes to inhibit nucleus pulposus cell apoptosis and reduce intervertebral disc degeneration," Journal of Cellular and Molecular Medicine, 22(1):261-276, 2018.

Collas et al., "On the way to reprogramming cells to pluripotency using cell-free extracts," Reproductive BioMedicine Online, 12(6):762-770, 2006.

Defendi-Cho et al., "In vitro culture of bovine fibroblasts using select serum-free media supplemented with Chlorella vulgaris extract," BMC Biotechnology, 23(4):1-11, 2023.

Denu et al., "Fibroblasts and Mesenchymal Stromal/Stem Cells are Phenotypically Indistinguishable," Acta Haematol., 126:85-97, 2016.

Ejiri et al., "Use of synthetic serum-free medium for culture of human dermal fibroblasts to establish an experimental system similar to living dermis," Cytotechnology, 67(3):507-514, 2015.

Elston et al., "Skin biopsy," J. Am. Acad. Dermatol., 74(1):1-16, 2016.

Extended European Search Report issued in European Patent Application No. 19795797.0, dated Oct. 21, 2021.

Extended European Search Report issued in European Patent Application No. 19796689.8, dated Nov. 25, 2021.

GIBCO Certificate of Analysis, KnockOut DMEM, 1 page, 2023.

Hu et al., "Exosomes secreted by human-induced pluripotent stem cell-derived mesenchymal stem cells attenuate limb ischemia by promoting angiogenesis in mice", Stem Cell Research & Therapy, 6(1):10, 2015.

Huangfu et al., "Induction of pluripotent stem cells by defined factors is greatly improved by small molecule compounds," Nat. Biotechnol., 26(7):795-797, 2008.

Im et al., "Repair of cartilage defect in the rabbit with cultured mesenchymal stem cells from bone marrow," J. Bone Joint Surg., 83-B(2):289-94, 2001.

International Search Report and Written Opinion for Application No. PCT/US2018/028358, mailed Jul. 6, 2018, 8 pages.

International Search Report and Written Opinion for Application No. PCT/US2019/030570, mailed Jul. 17, 2019, 12 pages.

International Search Report and Written Opinion for Application No. PCT/US2019/030577, mailed Jul. 5, 2019, 12 pages.

Jeong et al., "Effect of Concentrated Fibroblast-Conditioned Media on In Vitro Maintenance of Rat Primary Hepatocyte," PLoS ONE, 11(2):e0148846, pp. 1-14, 2016.

Jung et al., "Reprogram or Reboot: Small Molecule Approaches for the Production of Induced Pluripotent Stem Cells and Direct Cell Reprogramming," ACS Chemical Biology, 9:80-95, 2014.

Kalluri et al., "The biology, function, and biomedical applications of exosomes," Science, 367:1-15, 2020.

Kato et al., "Exosomes from IL-1 [beta] stimulated synovial fibroblasts induce osteoarthritic changes in articular chondrocytes", Arthritis Research & Therapy, 16(R163):1-11, 2014.

Kirschner et al., "Oxygen," Ullmann's Encyclopedia of Industrial Chemistry, pp. 1-32, 2017.

Kwon et al., "Depudecin induces morphological reversion of transformed fibroblasts via the inhibition of histone deacetylase," Proceedings of the National Academy of Sciences, 95:3356-3361, 1998.

Lai et al., "Efficient Generation of Chemically Induced Mesenchymal Stem Cells from Human Dermal Fibroblasts," Scientific Reports, 7:44534, 13 pages, 2017.

Lamparski et al., "Production and characterization of clinical grade exosomes derived from dendritic cells," Journal of Immunological Methods, 270:211-226, 2002.

Liu et al., "Mouse embryonic fibroblast (MEF)/BMP4-conditioned medium enhanced multipotency of human dental pulp cells," Journal of Molecular History, 49:17-26, 2018.

Masuda et al., "Osteogenic protein-1 injection into a degenerated disc induces the restoration of disc height and structural changes in the rabbit anular puncture model," Spine, 31(7):742-754, 2006.

Mathieu et al., "Hypoxia-inducible Factors Have Distinct and Stage-Specific Roles during Reprogramming of Human Cells to Pluripotency," Cell Stem Cell, 14:592-605, 2014.

Merriam-Webster, "Dedifferentiation," definition. Available at https://www.merriam-webster.com/dictionary/dedifferentiation?utm_campaign=sd&utm_medium=serp&utm_source=jsonld. 1 page. Accessed Oct. 23, 2024.

Obokata et al., "Stimulus-triggered fate conversion of somatic cells into pluripotency," Nature, including Extended Data and Retraction, 505:641-647, 2014.

Pilkus et al., "Fibroblasts: origins definitions, and functions in health and disease," Cell, 184(15):3852-3872, 2021.

Sakai et al., "Regenerative effects of transplanting mesenchymal stem cells embedded in atelocollagen to the degenerated intervertebral disc," Biomaterials, 27(3):335-345, 2006.

Salci et al., "Acquisition of pluripotency through continued environmental influence on OCT4-induced plastic human fibroblasts," Stem Cell Research, 15:221-230, 2015.

Satoh et al., "Regulation of dermal fibroblast dedifferentiation and redifferentiation during wound healing and limb regeneration in the Axolotl," Develop. Growth Differ., 50:743-754, 2008.

Shamis et al, "Fibroblasts Derived from Human Pluripotent Stem Cells Activate Angiogenic Responses in Vitro and in VivO", PLOS ONE, 8(12):e83755, 2013.

Sklirou et al., "6-bromo-indirubin-31-oxime (6BI0), a Glycogen synthase kinase-3[beta] inhibitor, activates cytoprotective cellular modules and suppresses cellular senescence-mediated biomolecular damage in human fibroblasts," Scientific Reports, 7(11713), 13 pages, 2017.

Soundarajan et al., "Fibroblasts and mesenchymal stem cells: Two sides of the same coin?" J. Cellular Physiology, 233:9099-9109, 2018.

Tam et al., "A Comparison of Intravenous and Intradiscal Delivery of Multipotential Stem Cells on the Healing of Injured Intervertebral Disk," Journal of Orthopaedic Research, 32:819-825, 2014.

Tang et al., "Fetal bovine serum albumin inhibits antimicrobial peptide activity and binds drug only in complex with α1-antitrypsin," Scientific Reports, 11(1):1267, 13 pages, 2021.

ThermoFisher Scientific Technical Resources: DMEM, high glucose recipe. Accessed Dec. 1, 2023 from URL: https://www.thermofisher.com/us/en/home/technical-resources/media-formulation.8.html. 2 pages.

ThermoFisher, Human Fibroblast Expansion Medium (formerly Medium 106) User Guide. Available at https://assets.fishersci.com/TFS-Assets/LSG/manuals/M106_man.pdf. 2 pages. Accessed Oct. 23, 2024.

(56) References Cited

OTHER PUBLICATIONS

ThermoFisher, Low Serum Growth Supplement (LSGS) User Guide. Available at https://assets.fishersci.com/TFS-Assets/LSG/manuals/LSGS_LSGS_Kit_man.pdf. 1 page. Accessed Oct. 23, 2024.

Ural et al., "Fibroblast Transplantation Results to the Degenerated Rabbit Lumbar Intervertebral Discs," The Open Orhopaedics Journal, 11(1):404-416, 2017.

Van Der Valk et al., "Fetal Bovine Serum (FBS): Past-Present-Future," ALTEX, 35(1):99-118, 2018.

Vedicherla et al., "Cell-based therapies for intervertebral disc and cartilage regeneration—Current concepts, parallels, and perspectives," Journal of Orthopaedic Research, 35(1):8-22, 2016.

Wang et al, "Exosomes/microvesicles from induced pluripotent stem cells deliver cardioprotective miRNAs and prevent cardiomyocyte apoptosis in the ischemic myocardium", International Journal of Cardiology, 192:61-69, 2015.

Webber et al., "Cancer Exosomes Trigger Fibroblast to Myofibroblast Differentiation", Cancer Research, 70(23):9621-9630, 2010.

Yoshida et al., "Hypoxia Enhances the Generation of Induced Pluripotent Stem Cells," Cell Stem Cell, 5:237-241, 2009.

Cheng et al., "The Potential of Neural Stem Cell as Vehicle to Deliver Quercus infecloria Extract to Glioma Cell In Vitro", Sains Malaysiana, 47(6):1209-1219, 2018.

Valencia et al., "Exosomes in Liquid Biopsy: The Nanometric World in the Pursuit of Precision Oncology", Cancers, 13(2147):1-16, 2021.

Wang et al., "L-Cysteine Promotes the Proliferation and Differentiation of Neural Stem Cells via the CBS/H2S Pathway", Neuroscience, 237:106-117, 2013.

Yang et al., "Hydrogen Sulfide Regulates Homeostasis of Mesenchymal Stem Cells and Regulatory T Cells", Journal of Dental Research, 95(13):1445-1451, 2016.

Zhu et al., "CD45RB Is a Novel Molecular Therapeutic Target to Inhibit Aβ Peptide-Induced Microglial MAPK Activation", PLoS One, 3(5):e2135, 12 pages, 2008.

Rajasingh et al., "Cell-free Embryonic Stem Cell Extract-Mediated Derivation of Multi-potent Stem Cells from NIK3T3 Fibroblasts for Functional and Anatomical Ischemic Tissue Repair." Nature Proceedings, 102(11), 1-24, 2008.

Bach et al., "Notochordal-cell derived extracellular vesicles exert regenerative effects on canine and human nucleus pulposus cells." Oncotarget, 8(51), 88845-88856, 2017.

* cited by examiner

1A NONcNZO10/LtJ mice- A polygenic strain with a leptin receptor gene mutation, developed to realistically model human metabolic syndrome and obesity-induced type 2 diabetes Normal diet:
- 15% protein
- 3% fat
- 7% carbohydrates High fat diet(F3282 pellets):
- 20.5% protein
- 36% fat
- 35.7% carbohydrates 1B Random blood glucose Glucose (mg/dL)
0
100
200
300
400
Baseline
12 weeks
14 weeks
16 weeks
17 weeks
18 weeks
Age Wound considered closed with the release of the scab and appearance of epithelialization.

- Treated mice: Fully closed wound at day 13-14.
- Control mice: Closed wound at day 20-21.

| | Control Matrigel | FB (Subcutaneous) | FB (Topical) | FB Exosomes |
|---|---|---|---|---|
| Control Matrigel | | *** | **** | **** |
| FB (Subcutaneous) | | | * | NS |
| FB (Topical) | | | | NS |

Red boxes indicate release of scab and appearance of epithelialization

| | Control Matrigel (N=8) | FB Exosomes (N=8) | FB Lysate (N=8) |
|---|---|---|---|
| Control Untreated (N=4) | NS | **** | **** |
| Control Matrigel (N=8) | | **** | *** |
| FB Exosomes (N=8) | | | NS |

Red boxes indicate release of scab and appearance of epithelialization

Arrows indicate scab release and visible epithelialization days

THERAPEUTIC USE OF FIBROBLASTS FOR USE IN WOUND HEALING

This application claims priority to U.S. Provisional Patent Application Ser. No. 63/320,388, filed Mar. 16, 2022; U.S. Provisional Patent Application Ser. No. 63/379,220, filed Oct. 12, 2022; and to U.S. Provisional Patent Application Ser. No. 63/383,498, filed Nov. 13, 2022, all of which are incorporated by reference herein in their entirety.

BACKGROUND

I. Technical Field

Embodiments of the disclosure concern at least the fields of cell biology, molecular biology, immunology, and medicine.

II. Background

Fibroblasts are no longer considered mere structural components of organs but as dynamic participants in multiple systems, such as the immune system and the complex interplay of multiple systems involved in wound healing.

Skin is the largest organ in the human body encompassing about 15% of the total body weight, and serves multiple complex functions such as protection from external physical, chemical, and microbial impacts; maintenance of temperature and electrolyte balance; serving as a biofactory for the synthesis and metabolism of structural proteins, lipids, glycans, and signaling molecules; as well as an integral component of the immune, nervous, and endocrine systems [1]. As such, injury to the skin and the repair process to the skin is a well-tuned process involving multiple systems and cell types. Wound healing follows an intricately orchestrated process of haemostasis, inflammation, proliferation, epithelialization, and remodeling confined to the injury location [2].

Wound treatment forms a significant burden to the healthcare system and destroys quality of life for the victims of nonhealing wounds. Difficult-to-heal wounds, including chronic wounds, are persistent, time-consuming, and costly to treat. In addition, injury to the skin because of diseases (such as diabetes or cancer), cuts, abrasions, bedsores, or burns can have a lasting impact on the physical, emotional, and psychological wellbeing of a patient. While some injuries caused to the skin can heal normally and quickly, certain underlying health aspects such as age, health status, and certain diseases can adversely impact the intricately orchestrated wound healing process, thereby requiring external intervention to heal properly.

SUMMARY

Embodiments of the disclosure encompass compositions, methods, and systems for introducing activated or inactivated fibroblasts, and/or fibroblast-derived materials (including fibroblast cells; fibroblast-like cells; and/or extracellular vesicles including exosomes, microvesicles, apoptotic bodies, or a combination thereof, or any other fragments or biologic components of fibroblast cells), onto and/or into wounds, with or without other types of cells, such as keratinocytes and/or epithelial cells. The cells and/or cell-derived products (including cells and/or extracellular vesicles including exosomes, microvesicles, apoptotic bodies or any other fragments or biologic components of fibroblast cells) can be used at a wound site in any suitable form, including at least as a spray, gel, suspension, by mechanical application, on a device, in a gel matrix, included within a synthetic or organic polymer matrix, as 3D-cultured cells, and/or 3D-printed matrix, including comprising one or more cell types in some embodiments. In some cases, one or more additional agents, such as one or more growth factors, one or more cytokines, one or more chemokines, and/or one or more activating factors may be administered onto the wound site and/or around the wound site and/or may be in or inside the surrounding tissue. In such cases, the additional agent(s) may or may not be provided to the wound site(s) in the same formulation or in the same manner as the activated or inactivated fibroblasts, and/or fibroblast-derived materials (including fibroblast cells; fibroblast-like cells; and/or extracellular vesicles including exosomes, microvesicles, apoptotic bodies, fibroblast cell lysate, or a combination thereof, or any other fragments or biologic components of fibroblast cells)

In particular embodiments, the disclosure concerns or encompasses the interaction of a first type of cells or cell derivatives (including fibroblast cells; fibroblast-like cells; and/or extracellular vesicles including exosomes, microvesicles, apoptotic bodies, fibroblast cell lysate, or any other fragments or biologic components of fibroblast cells) with a second type of cells and/or certain agent(s) and includes modification(s) to the first and/or second type of cells as a result of the interaction. In addition, in specific embodiments, the disclosure includes compositions, methods, and systems in which fibroblasts (including fibroblast cells; fibroblast-like cells; and/or extracellular vesicles including exosomes, microvesicles, apoptotic bodies or any other fragments or biologic components of fibroblast cells) are modified upon exposure to certain cells and/or one or a combination of certain agent(s), including nucleic acids, cytokines, chemokines, and/or growth factors. In certain embodiments, introduction of these modified or unmodified fibroblasts (including fibroblast cells; fibroblast-like cells; and/or extracellular vesicles including exosomes, microvesicles, apoptotic bodies or any other fragments or biologic components of fibroblast cells) onto and/or into the wound and in some cases surrounding tissue can initiate the process of proliferation, epithelialization, and attraction of other biologic processes that aid in healing and remodeling necessary for wound healing, such as by regenerating the necessary functional cells, including myofibroblasts, vascular epithelial cells, human dermal fibroblasts, and/or by regenerating extracellular matrix materials, such as Collagen I-XIV, Fibrin, fibronectin, vitronectin, elastin, hyaluronan, chondroitin sulfate, decorin, versican, SPARC, and/or tenascin[3].

In certain embodiments, the regeneration of these cells and cell components at the wound site can be either through one or more several possible steps such as:

(1) The injection of the modified or unmodified fibroblasts (including fibroblast cells; fibroblast-like cells; and/or extracellular vesicles including exosomes, microvesicles, apoptotic bodies or any other fragments or biologic components of fibroblast cells) into the wound area[4] or applied topically to the wound and surrounding tissue.

(2) Recruitment of neutrophils, macrophages, and platelets to the wound by the fibroblasts[5] (including fibroblast cells; fibroblast-like cells; and/or extracellular vesicles including exosomes, microvesicles, apoptotic bodies or any other fragments or biologic components of fibroblast cells).

(3) Activating the patient-senescent human dermal fibroblasts (including fibroblast cells; fibroblast-like cells; and/or extracellular vesicles including exosomes, microvesicles, apoptotic bodies or any other fragments or biologic components of fibroblast cells), keratinocytes, vasal epithelial cells, and/or myofibroblasts through cell-to-cell (paracrine) contact with modified or unmodified fibroblasts[6] (including fibroblast cells; fibroblast-like cells; and/or extracellular vesicles including exosomes, microvesicles, apoptotic bodies or any other fragments or biologic components of fibroblast cells).

(4) Differentiation of local stem cells, human dermal fibroblasts (including fibroblast cells; fibroblast-like cells; and/or extracellular vesicles including exosomes, microvesicles, apoptotic bodies or any other fragments or biologic components of fibroblast cells), keratinocytes, vasal epithelial cells, and/or myofibroblasts through the direct/indirect action of the introduced modified/unmodified fibroblasts or excreted products from the modified/unmodified fibroblasts.

(5) Expansion of endogenous human dermal fibroblasts (including fibroblast cells; fibroblast-like cells; and/or extracellular vesicles including exosomes, microvesicles, apoptotic bodies or any other fragments or biologic components of fibroblast cells, and also including an individual's own fibroblasts that have become senescent), keratinocytes, vasal epithelial cells, and/or myofibroblasts cells remaining in the injured skin to initiate the wound healing process.

(6) Initiation of angiogenesis by direct and/or indirect interaction of the introduced fibroblasts and/or fibroblast-excreted materials[7].

(7) Recruitment of stem cells and any other cells useful for the healing process to the injury site by the direct and/or indirect actions of the introduced fibroblasts and/or material excreted by the introduced fibroblasts [8].

In specific embodiments, the disclosure concerns compositions, methods, and systems in which certain cells are modified upon exposure to fibroblasts (including fibroblast cells; fibroblast-like cells; and/or extracellular vesicles including exosomes, microvesicles, apoptotic bodies or any other fragments or biologic components of fibroblast cells) and/or certain agent(s) excreted from fibroblasts, or contained within the fibroblasts. In particular embodiments, the interaction of fibroblasts (including fibroblast cells; fibroblast-like cells; and/or extracellular vesicles including exosomes, microvesicles, apoptotic bodies or any other fragments or biologic components of fibroblast cells) with one or more other types of cells (and optionally that interaction also includes one or more certain agent(s)) results in modification of the fibroblasts and/or the other type of cells involved in wound healing. In specific embodiments, the other types of cells include at least recruited immune cells (e.g., dendritic cells, neutrophils, monocytes, macrophages, NK cells, T cells, mast cells, and sin-resident T cells) and local stem cells[8].

In certain embodiments, the introduction of live single cell suspension, live multi-cell suspension, live 3D spheroid fibroblasts, inactivated fibroblasts, dead fibroblasts, and/or fibroblast-derived materials to the wound results in the modification of fibroblasts and other cells found in the wound and/or surrounding tissue to stimulate wound repair. In certain aspects, prior or present exposure of fibroblasts and/or agents derived from fibroblasts, or produced therefrom (including fibroblast cells; fibroblast-like cells; and/or extracellular vesicles including exosomes, microvesicles, apoptotic bodies or any other fragments or biologic components of fibroblast cells), results in modifications to one or more types of cells present in the injury site. In specific embodiments, one or more agents are also included in the exposure and may or may not be exogenously provided, such as in other cases where they are endogenous to an environment and/or cell and/or tissue.

In specific embodiments, methods of the disclosure occur ex vivo, such as in a culture, and such as ex vivo activating/inactivating of fibroblast cells, or other cells in the treatment, prior to application on the wound. In particular cases, the methods occur by the hand of man and do not encompass ordinary or random occurrences in a body. The methods of the disclosure are non-natural, in particular aspects. In specific embodiments, the concentrations of cells or cell-derived materials (including fibroblast cells; fibroblast-derived lysate; fibroblast-like cells; and/or extracellular vesicles including exosomes, microvesicles, apoptotic bodies or any other fragments or biologic components of fibroblast cells) used in a method of exposing one type of cells to another type of cells do not occur in nature and do not happen randomly in nature.

The lack of natural exposure in diabetics because of the metabolic and immune deficiencies may be one explanation for nonhealing or difficult-to-heal chronic wounds of theirs. In specific embodiments, the concentration of one or more agents used in a method of exposing one or more agents to one or more types of cells does not occur in nature and does not happen randomly in nature. The modification of any types of cells encompassed by the disclosure that occurs ex vivo or in vitro does not occur in vivo naturally in the same manner. In such embodiments, tissue biopsy from the donor is used to isolate, characterize, if necessary, activate, expand, and reintroduce back into the donor one or a combination of the cells for the purpose of wound repair.

The disclosure encompasses therapeutic uses of cells, including epithelial cells, neutrophils, macrophages, keratinocytes, vasal epithelial cells, fibroblasts (including myofibroblasts), and mixtures thereof. In at least some cases, the fibroblasts or fibroblast-derived materials (including fibroblast cells; fibroblast-like cells; and/or extracellular vesicles including exosomes, microvesicles, apoptotic bodies or any other fragments or biologic components of fibroblast cells) have been modified prior to their exposure to the wound site, such as chemically, genetically, virally, physically, mechanically, epigenetically-activated, and/or exposed to conditions not normally found in the body. In other cases, neutrophils, macrophages, keratinocytes, vasal epithelial cells, myofibroblasts, or their derivatives, have been modified, such as activated, prior to their exposure to the fibroblasts.

Embodiments of the disclosure provide means of utilizing fibroblasts as allogeneic, autologous (or xenogeneic or syngeneic) therapeutic cells through modification of culture conditions. In one embodiment of the disclosure, fibroblasts (including fibroblast cells; fibroblast-like cells; and/or extracellular vesicles including exosomes, microvesicles, apoptotic bodies or any other fragments or biologic components of fibroblast cells) are extracted from sources with lower immunogenicity (e.g., placental fibroblasts, omental tissue-derived fibroblasts, cord blood-derived fibroblasts, etc.). In one embodiment of the disclosure, fibroblasts (including fibroblast cells; fibroblast-like cells; and/or extracellular vesicles including exosomes, microvesicles, apoptotic bodies or any other fragments or biologic components of fibroblast cells) are extracted from the skin or any other region of the body where the biologic healing process derived from the fibroblasts prove efficacious.

In one embodiment of the disclosure, fibroblasts (including fibroblast cells; fibroblast-like cells; fibroblast-derived lysate; and/or extracellular vesicles including exosomes, microvesicles, apoptotic bodies or any other fragments or biologic components of fibroblast cells) are cultured in vitro for preserving the viability and proliferative ability of fibroblasts. The disclosure provides for the modification of known culture techniques to decrease the recognition of fibroblasts by the recipient immune system. In one embodiment, fibroblasts(including fibroblast cells; fibroblast-like cells; and/or extracellular vesicles including exosomes, microvesicles, apoptotic bodies or any other fragments or biologic components of fibroblast cells) are cultured in conditions that lack xenogeneic components, such as xenogeneic-free medium. In some cases, for example, the media is free of fetal calf serum. In specific embodiments, the disclosure encompasses the substitution of fetal calf serum with one or more other agents, such as those that facilitate reduction of immunogenicity of fibroblasts, for example, human platelet-rich plasma, platelet lysate, umbilical cord blood serum, autologous serum, and/or one or more defined cytokines, such as one or a combination of fibroblast growth factor, epidermal growth factor, leukemia inhibitory factor, insulin-like growth factor, angiopoietin, and vascular endothelial growth factor.

In one embodiment of the disclosure, effective amounts of fibroblasts (including fibroblast cells; fibroblast-like cells; and/or extracellular vesicles including exosomes, microvesicles, apoptotic bodies or any other fragments or biologic components of fibroblast cells) as prepared in methods encompassed by the disclosure are administered to an individual for therapy or prevention of one or more medical conditions. In specific embodiments, the fibroblasts and/or fibroblast-derived materials are administered to improve wound repair, proliferation, cell differentiation, and tissue remodeling.

Embodiments of the disclosure provide methods for co-administration of universal donor fibroblasts or autologously modified with one or more agents that stimulate and maintain the wound repair process. In a specific embodiment of the disclosure, methods are provided for co-administration of universal donor fibroblasts and/or fibroblast-derived materials with one or a combination of growth factors, chemokines, cytokines, and/or growth factors. In one embodiment of the disclosure, universal donor fibroblasts derived from fibroblasts that have been treated under conditions to reduce immunogenicity are utilized to stimulate fibroblast growth factors required for wound healing, such as EGF, FGF-2, TGF-Beta, PDGF, VEGF, IL-1, IL-6, and/or TNF-alpha by the introduced modified/unmodified fibroblasts or from endogenous cells, thereby leading to tissue regeneration and healing of the wound[10].

Embodiments of the disclosure provide methods of reducing the immunogenicity of particular types of fibroblasts. Fibroblasts may be derived from various tissues or organs, including but not limited to skin, heart, blood vessels, bone marrow, skeletal muscle, liver, pancreas, brain, foreskin, which can be obtained by biopsy (where appropriate) or upon autopsy. In some aspects, the cells comprise fibroblasts, which can be from a fetal, neonatal, adult origin, or a combination thereof.

Fibroblasts for use in any methods of the disclosure may be exposed to certain medium component(s) in specific embodiments.

The foregoing has outlined rather broadly the features and technical advantages of the present invention so that the detailed description of the invention that follows may be better understood. Additional features and advantages of the invention will be described hereinafter, which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages, will be better understood from the following description when considered in connection with the accompanying figures. It is to be expressly understood, however, that each of the figures is provided for the purpose of illustration and description only and is not intended as a definition of the limits of the present invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION

I. Examples of Definitions

Figure 1A:
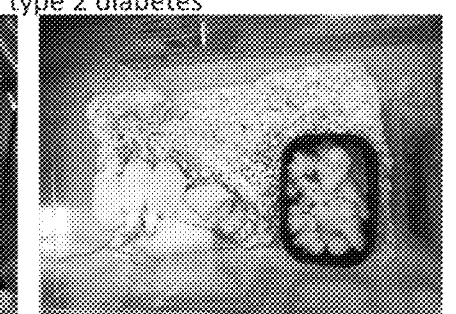
FIG. 1A demonstrates the diet components of the mice model of human metabolic syndrome and obesity-induced type 2 diabetes.

Throughout this application, the term "about" is used to indicate that a value includes the inherent variation of error for the measurement or quantitation method.

The use of the word "a" or "an" when used in conjunction with the term "comprising" may mean "one," but it is also consistent with the meaning of "one or more," "at least one," and "one or more than one."

As used herein, the term "about" or "approximately" refers to a quantity, level, value, number, frequency, percentage, dimension, size, amount, weight, or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%. With respect to biological systems or processes, the term can mean within an order of magnitude, such as within 5-fold, and such as within 2-fold, of a value. Unless otherwise stated, the term 'about' means within an acceptable error range for the particular value.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

Throughout this application, the term "about" is used according to its plain and ordinary meaning in the area of cell and molecular biology to indicate that a value includes the standard deviation of error for the device or method being employed to determine the value.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "comprising," which is synonymous with "including," "containing," or "characterized by," is inclusive or open-ended and does not exclude additional, unrecited elements or method steps. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of."

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein and that different embodiments may be combined.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "activated fibroblasts" refers to any kind of fibroblasts treated with one or more stimuli or agent(s) capable of inducing one or more alterations in the fibroblast: metabolic, immunological, epigenetic, growth factor-secreting, surface marker expression, and production and excretion of microvesicles. Examples of agents include at least ADP, CXCL4, PDGF, TGFβ, IL-1, TNFα, ROS, NO, AMP, IL-17, IL22, dsRNA 1.25D3, IL-8, CXCL1-8, Activin A, β-defensins, cathelicidin, E-selectin, P-selectin, KGF, VEGF, IGF, IL-10, IL-4, and IL-13.

As used herein, the term "activated immune cells" refers to immune cells treated with one or more stimuli or agent(s) capable of inducing one or more alterations in the cell: metabolic, immunological, epigenetic, growth factor-secreting, surface marker expression, and production and excretion of microvesicles. Examples of agents include at least ADP, CXCL4, PDGF, TGFβ, IL-1, TNFα, ROS, NO, AMP, IL-17, IL22, dsRNA 1.25D3, IL-8, CXCL1-8, Activin A, β-defensins, cathelicidin, E-selectin, P-selectin, KGF, VEGF, IGF, IL-10, IL-4, and IL-13.

The term "administered" or "administering," as used herein, refers to any method of providing a composition to an individual such that the composition has its intended effect on the patient. For example, one method of administering is by an indirect mechanism using a medical device such as, but not limited to, a catheter, applicator gun, syringe, gel matrix, cells or cell products loaded onto a synthetic or biopolymer, and a 3D matrix containing one or more cell types, cell-derived products and or growth factors and or antibiotics, etc. A second exemplary method of administering is by a direct mechanism such as local tissue administration, oral ingestion, transdermal patch, topical, inhalation, suppository, etc.

As used herein, "allogeneic" refers to tissues or cells from another body that in a natural setting are immunologically incompatible or capable of being immunologically incompatible, although from one or more individuals of the same species.

As used herein, "autologous" refers to tissues or cells that are derived or transferred from the same individual's body (i.e., autologous blood donation; an autologous bone marrow transplant).

As used herein, "agent" refers to nucleic acids, cytokines, chemokines, transcription factors, epigenetics factors, growth factors, hormones, or a combination thereof including whole cell lysate.

As used herein, "xenogeneic" refers to tissues or cells from a species different from the patient.

"Cell culture" is an artificial in vitro system containing viable cells, whether quiescent, senescent, or (actively) dividing. In a cell culture, cells are grown and maintained at an appropriate temperature, typically a temperature of 37° C. and under an atmosphere typically containing oxygen and $CO_2$ at various concentrations. Culture conditions may vary widely for each cell type, though, and variation of conditions for a particular cell type can result in different phenotypes being expressed. The most commonly varied factor in culture systems is the growth medium, and oxygen concentration during culturing. Growth media can vary in concentration of nutrients, growth factors, and the presence of other components. The growth factors used to supplement media are often derived from animal blood, such as calf serum.

The term "individual," as used herein, refers to a human or animal that may or may not be housed in a medical facility and may be treated as an outpatient of a medical facility. The individual may be receiving one or more medical compositions via the internet. An individual may comprise any age of a human or non-human animal and therefore includes both adult and juveniles (i.e., children) and infants. It is not intended that the term "individual" connotes a need for medical treatment, therefore, an individual may voluntarily or involuntarily be part of experimentation, whether clinical or in support of basic science studies. The term "subject" or "individual" may be used interchangeably and refers to any organism or animal subject that is an object of a method or material, including mammals, e.g., humans, laboratory animals (e.g., primates, rats, mice, rabbits), livestock (e.g., cows, sheep, goats, pigs, turkeys, and chickens), household pets (e.g., dogs, cats, and rodents), horses, and transgenic non-human animals.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

The terms "reduce," "inhibit," "diminish," "suppress," "decrease," "prevent," and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

As used herein, the term "transplantation" refers to the process of taking living tissue or cells and implanting it in another part of the body or into another body.

As used herein, the term "therapeutically effective amount" is the amount of a composition provided to an individual such that a wound is improved in severity and/or size (including diameter or area).

"Treatment," "treat," or "treating" means a method of reducing the effects of a disease or condition. Treatment can also refer to a method of reducing the disease or condition itself rather than just the symptoms. The treatment can be any reduction from pre-treatment levels and can be but is not limited to the complete ablation of the disease, condition, or the symptoms of the disease or condition. Therefore, in the disclosed methods, treatment" can refer to a 10%, 20%, 30%, 40%, 50%, 60%, 70%, 80%, 90%, or 100% reduction in the severity of an established disease or the disease progression, including a reduction in the severity of at least one symptom of the disease. For example, a disclosed method for reducing the immunogenicity of cells is considered to be a treatment if there is a detectable reduction in the immunogenicity of cells when compared to pre-treatment levels in the same subject or control subjects. Thus, the reduction can be a 10, 20, 30, 40, 50, 60, 70, 80, 90, 100%, or any amount of reduction in between as compared to native or control levels. It is understood and herein contemplated that "treatment" does not necessarily refer to a cure of the disease or condition but an improvement in the outlook of a disease or condition. In specific embodiments, treatment refers to the lessening in severity or extent of at least one symptom and may alternatively or in addition refer to a delay in the onset of at least one symptom.

In specific embodiments, externally-applied fibroblasts and/or fibroblast-derived materials (including fibroblast cells; fibroblast-like cells; fibroblast-derived lysate; and/or extracellular vesicles including exosomes, microvesicles, apoptotic bodies or any other fragments or biologic components of fibroblast cells) on wounds can initiate, maintain, and accelerate the wound healing process in wounds of any kind, including in diabetic ulcers, non-healing wounds, surgical incisions, traumatic injuries, abrasions, skin disorders, cuts, and burns. As used herein, the term "wound" encompasses an injury to living tissue, for example caused by a cut, blow, or other impact, typically one in which the skin is cut or broken. In specific embodiments, all of the above-mentioned conditions are wounds that would require healing.

The term "fibroblast-derived material" as used herein refers to fibroblast cell fragments, conditioned media, exosomes secreted from fibroblasts, and/or fibroblast lysate and includes fibroblast-like cells; and/or extracellular vesicles including exosomes, microvesicles, apoptotic bodies or any other fragments or biologic components of fibroblast cells.

The term "fibroblast-like cell" refers to cells that share certain characteristics features of fibroblasts, but exhibits surface markers, structural features, expression patterns, and epigenetic profiles similar to the cells they are closely associated with in a specific location. Some example include myofibroblasts, perineurial sheath cells, lymphoid organ dendritic cells, and villas fibroblasts in the intestine.

Embodiments of the disclosure encompass use of cells and/or cell products for wound healing, including to initiate and/or maintain wound healing. In some embodiments, the cells and/or cell products prior to, or during, use for wound healing are exposed to one or more compositions and/or environments to enhance their use in wound healing. In specific embodiments, cells and/or cell products are exposed in an in vitro setting to produce activated fibroblasts, fibroblast-derived materials from activated fibroblasts, activated immune cells, activated keratinocytes, activated vasal epithelial cells, activated myofibroblasts or fibroblast derivatives therefrom, including for introduction into, on top of, and/or adjacent to the wound to initiate and or maintain wound healing. In some embodiments, cells that are used have not been activated.

Embodiments of the disclosure include introduction of fibroblasts or fibroblast-derived materials (including fibroblast cells; fibroblast-like cells; and/or extracellular vesicles including exosomes, microvesicles, apoptotic bodies or any other fragments or biologic components of fibroblast cells), fibroblasts activated with one or more agents, and/or fibroblasts (including myofibroblasts or dermal fibroblasts) plus one or more types of immune cells, keratinocytes, and/or vasal epithelial cells and/or derivatives thereof into, on top of, and/or adjacent to the wound for the purpose of initiating or maintaining wound healing.

Methods of the disclosure may be utilized for any abrasion (wound caused by friction when a body scrapes across a rough surface), avulsion (characterized by a flap), incision (a cut with clean edges), laceration (cut with jagged edges), or puncture wound (a wound where something passes through or becomes impaled in the skin. The wound may or may not be infected with a pathogen, and in cases where it is infected one or more antibiotics may be used at the wound and/or systemically in the individual. In such cases, the antibiotic and compositions encompassed herein may or may not be administered at the same time and may or may not be in the same composition. The wound may be a Class 1, 2, 3, or 4 wound as classified by the U.S. Center for Disease Control.

In various embodiments, introduction of fibroblasts and/or fibroblast-derived materials (including fibroblast cells; fibroblast-like cells; and/or extracellular vesicles including exosomes, microvesicles, apoptotic bodies or any other fragments or biologic components of fibroblast cells), fibroblasts activated with one or more agents, and/or fibroblasts plus one or more type of immune cells (including derivatives thereof and that may be activated) into, on top of, and/or adjacent to the wound site results in partial or full healing, for example results in (1) tissue differentiation; (2) cell recruitment and differentiation of stems cells at the wound site; (3) expansion of already locally present keratocytes, vasal epithelial cells, myofibroblasts, and/or dermal fibroblasts; and/or (4) attraction of other cells or biologic processes to aid in the healing, all for the purpose of initiating or maintaining wound healing. In specific embodiments, the healing of the wound by any mechanism occurs at a faster rate than the healing of the wound in the absence of the disclosed methods or compositions.

In particular embodiments, fibroblasts (including fibroblast cells; fibroblast-like cells; and/or extracellular vesicles including exosomes, microvesicles, apoptotic bodies or any other fragments or biologic components of fibroblast cells) or other cells encompassed herein become activated following exposure to one or more conditions and/or agents. Specific agents that may modify the fibroblasts include one or more of nucleic acids, cytokines, chemokines, growth factors, and/or exosomes prior to and/or during their use. The fibroblast cells may be activated, such as having activated or engineered surface markers, nucleic acid modification, and/or expression or excretion of one or more chemokines, one or more cytokines, exosomes, and/or one or more growth factors. The cells may be activated by one or more chemical agents, RNA, micro RNA, RNAi, DNA, viral nucleic acid, and/or exosomes. In specific embodiments, the cytokine is selected from the group consisting of IFN-gamma, TNF-alpha, interleukin(IL)-1, IL-6, IL-7, IL-8, IL-12, IL-15, IL-17, IL-33, and a combination thereof. In specific embodiments, the growth factor is selected from the group consisting of FGF-1, VEGF, and a combination thereof. In specific embodiments, the cells are activated following exposure to human platelet rich plasma, platelet lysate, umbilical cord blood serum, autologous serum, human serum, serum replacement, or a combination thereof. In specific embodiments, the cells are activated following exposure to hypoxia. The hypoxia may be 0.1%-10%, 0.1%-5%, 0.1%-2.5%, or 0.1%-4% oxygen, for example. In specific embodiments, the hypoxia occurs for a period of time that is at least or no more than between about 30 minutes-about 3 days, although in some cases it may be less than 30 minutes or greater than 3 days. The fibroblasts may be exposed to one or more growth factors prior to and/or during exposure to hypoxia, carbon monoxide, or a combination thereof.

In some embodiments, fibroblasts or fibroblast-derived materials (including fibroblast cells; fibroblast-like cells; and/or extracellular vesicles including exosomes, microvesicles, apoptotic bodies or any other fragments or biologic components of fibroblast cells) are used with one or more adjuvants to activate the immune system and initiate and or maintain the wound healing process. These adjuvants could be chemical, mechanical, viral, genetically modified components, or bacterial products-based. Examples include at least aluminum hydroxide, aluminum phosphate, aluminum potassium sulfate monophosphoryl lipid A, Qs-21, cytosine phosphoguanine, saponin, and/or oil-in-water emulsions comprising squalene.

In specific embodiments, encapsulated RNA, microRNA, or RNAi, and/or fibroblast-derived exosomes or other microvesicles are utilized are utilized any other cell or cell fragments derived from fibroblasts, with fibroblasts locally initiating and maintaining the wound-healing process.

Embodiments of the disclosure include the use of fibroblasts or fibroblast-derived materials (including fibroblast cells; fibroblast-like cells; and/or extracellular vesicles including exosomes, microvesicles, apoptotic bodies or any other fragments or biologic components of fibroblast cells) in angiogenesis formation, repair, and/or regeneration in a wound site and surrounding tissue.

In particular embodiments, a therapeutically effective amount of spheroids may be applied to a wound. The amount may be dictated by the number of cells in the spheroid and/or the number of spheroids applied. As one example, for 8 mm diameter wounds, about 100 spheroids may be applied to the wound that equals about 3 million cells. In specific embodiments, at least about 1, 5, 10, 20, 30, 40, 50, 60, 70, 80, 90, 100, 150, 200, 250, 300, 400, 500, 750, or 1000 or more spheroids may be applied to a wound. The spheroids may comprise at least about 5,000, 10,000, 15,000, 20,000, 25,000, 30,000, 35,000, 40,000, 45,000, 50,000, 60,000, 70,000, 80,000, 90,000, 100,00, or more cells each.

In particular embodiments, a therapeutically effective amount of lysate, exosomes, etc., may be derived from a particular amount of fibroblast cells cultured in media. In specific embodiments, the amount of cultured fibroblast cells include at least 1, 2, 3, 4, 5, 6, 7, 8, 9, 10 million, or more cells. In specific cases, the number of cultured fibroblast cells to produce the lysate, exosomes, etc., is determined by the size of the wound being treated. In one embodiment, about an 8 mm wound is provided lysate or exosomes from 3 million fibroblast cells. In particular embodiments, the amount of material administered will depend on the size of the wound. In a specific embodiment, the amount of material administered is in the range of 30,000 to 100,000 cells, or materials derived from those number of cells, per $mm^2$.

In some embodiments, one or more compositions are present on, or are delivered on, a substrate comprising the compositions in the substrate, on the substrate, around the substrate, or a combination thereof. In other embodiments, the compositions is applied to the substrate at the site of need. In some embodiments, one or more compositions are utilized at the same wound or burn and may or may not employ the same type of substrate.

In specific embodiments of the composition, one or more substrate components of are comprised of a synthetic polymer and/or a biopolymer, and in specific cases the biopolymer is a natural polymer. The synthetic polymer and/or a biopolymer may be of any type so long as they are compatible for use on and/or in an individual. In embodiments wherein the substrate of the composition comprises biopolymers such as keratin, fibrin, collagen, cellulose, alginate, chitosan, cyanoflan, hyaluronic acid, and/or hydrogels. In embodiments wherein the polymer comprises one or more synthetic polymers, the synthetic polymer may be poly (ethylene glycol) (PEG)/poly(ethylene oxide)(PEO), poly (vinyl pyrrolidone) (PVP), poly(vinyl alcohol) (PVA), [15], poly(hydroxyethyl methacrylate) (PHEMA), polyurethanes (PUs), poly (α-esters) [e.g., poly(lactic-co-glycolic acid) (PLGA), polyglycolic acid (PGA), polylactide (PLA), and/or poly(F-caprolactone)(PCL). In embodiments wherein the polymer comprises one or more synthetic inorganic polymers such a PDMS, HPE, natural minerals, synthetic silicates, phosphates, zeolites, clay, sesoporous silica, polyP, and so forth.

The configuration parameters of the substrate, including at least size, substance, thickness, presence of any one or more demarcations, presence of any one or more apertures, shape, etc., may or may not be tailored to an intended wound/burn. In some embodiments, the substrate is tailored in configuration parameter(s) to the intended use of the composition, whereas in other cases the substrate is utilized in an off-the-shelf manner. In cases wherein the substrate is tailored for a specific use, the compositions may or may not already be present on the substrate. In cases wherein the substrate is not initially tailored and is to be utilized in an off-the-shelf manner, the compositions may or may not already be present on the substrate.

The shape of the outside border of the substrate may be random or may be of a particular shape, such as a square, rectangle, triangle, circle, trapezoid, rhombus, crescent, and so forth. Thus, the substrate may be a particular geometric formation. The width of the substrate that is applied at the site may depend on the width of the wound. The substrate may be reduced in size, such as tailored to the wound, prior to or after placement of the substrate at or on the wound. The size and shape of the substrate can be adjusted to wound size.

The substate may be a scaffolding, in some embodiments. In specific embodiments, the scaffolding as a structure that facilitates placement of the cells in single cell or spheroid format, inside the scaffolding, and allow for cell migration and/or cell proliferation, for example at the dermal layer, from the location where the cells are located. The scaffolding allows tissue growth, such as to mimic the biological process or structure for tissue engineering that is in need of being replaced, in some embodiments. The scaffolding may be fibrous, porous, or of a hydrogel, in specific embodiments.

In specific cases, the substrate is a tray, a cup, a mesh, and so forth. The substrate may be comprised of a biopolymer, organic or inorganic polymer fabric of any kind.

In specific embodiments, the substrate comprises one or multiple apertures, or perforations. The apertures, or perforations with respect to the substrate may be in a random pattern or in an ordered pattern. The size of the apertures may be configured to be big enough to allow efficient cell migration and to allow securing of one or more spheroids at the site.

In specific embodiments, there is introduction of single-cell or spheroid fibroblasts, exosomes from fibroblasts, lysate from fibroblasts, apoptotic bodies from fibroblasts, and/or fibroblast-related products or any combination thereof onto a substrate of any kind, such as a synthetic polymer or biopolymer scaffolding, tray, geometric formation, biologic fabric, mesh, or polymer fabric. The step(s) of applying the biologic component(s) to the substrate component, whether or not it is prior to placement at the wound or burn or at the time of placement at the wound or burn, may be of any suitable manner.

In specific embodiments, there is introduction of single-cell or spheroid fibroblasts, exosomes from fibroblasts, lysate from fibroblasts, or apoptotic bodies from fibroblasts and/or fibroblast-related products onto a synthetic polymer or biopolymer scaffolding, tray, geometric formation, biologic fabric, mesh, or polymer fabric using a device, such as a spreading device. Any spreading device referred to herein may be considered as an applicator.

In certain embodiments, there is introduction of single-cell or spheroid fibroblasts, exosomes from fibroblasts, lysate from fibroblasts, or apoptotic bodies from fibroblasts and/or fibroblast-related products onto a synthetic polymer or biopolymer scaffolding, tray, geometric formation, biologic fabric, mesh, or polymer fabric using a device, such as a spreading device, designed with one or more grooves.

In certain embodiments, there is introduction of single-cell or spheroid fibroblasts, exosomes from fibroblasts, lysate from fibroblasts or apoptotic bodies from fibroblasts and/or fibroblast-related products onto a synthetic polymer or biopolymer scaffolding, tray, geometric formation, biologic fabric, mesh, or polymer fabric using a device, such as a spreading device. In certain embodiments, the device is designed with an ordered pattern of holes to allow spheroid placement or with a random series of holes to allow randomized spheroid placement.

In some embodiments, there is introduction of single-cell or spheroid fibroblasts, exosomes from fibroblasts, lysate from fibroblasts, or apoptotic bodies from fibroblasts and/or fibroblast-related products onto a synthetic polymer or biopolymer scaffolding, tray, geometric formation, biologic fabric, mesh, or polymer fabric using a spray or misting device. In specific embodiments, the spray or misting device is utilized for uniformity of placement of the biological material onto a substrate.

In certain embodiments, there is introduction of single-cell or spheroid fibroblasts, exosomes from fibroblasts, lysate from fibroblasts, or apoptotic bodies from fibroblasts and/or fibroblast-related products onto a substrate comprising a synthetic polymer and/or biopolymer, such as a scaffolding, tray, geometric formation, biologic fabric, mesh, or polymer fabric, using a 3-D printer.

In specific embodiments, there is culturing of fibroblast spheroids inside the holes of a perforated synthetic or biopolymer in which the apertures are spaced in such a way as to accommodate the proliferation from a specific size and fibroblast cell number-containing spheroid onto a wound surface.

In some embodiments, there is dispensing of specific-sized fibroblast spheroids into the apertures of a synthetic and/or biopolymer substrate such that only one spheroid is placed in a single aperture to allow the proliferation of the fibroblasts onto the wound surface from the opposite side of the aperture.

In particular embodiments, there is use of a high-resolution camera to generate an image for the introduction of single-cell or spheroid fibroblasts, exosomes from fibroblasts, lysate from fibroblasts, or apoptotic bodies from fibroblasts and/or fibroblast-related products in a 3-D printer for the purpose of matching the boundaries of the wound being covered.

EXAMPLES

The following examples are included to demonstrate certain embodiments of the disclosure. It should be appreciated by those of skill in the art that the techniques disclosed in the examples which follow represent techniques discovered to function well in the practice of the invention, and thus can be considered to constitute particular modes for its practice. However, those of skill in the art should, in light of the present disclosure, appreciate that many changes can be made in the specific embodiments that are disclosed and still obtain a like or similar result without departing from the spirit and scope of the embodiments of the disclosure.

Example 1

Therapeutic Use of Fibroblasts for Use in Wound Healing

Introduction

Skin wound repair is essential for organismal survival and failure of skin would repair, which leads to non-healing wounds, is a leading health issue worldwide. Wound healing studies are intricate, mainly because of the wound environment's multifaceted nature and the healing process's complexity, which integrates a variety of cells and repair phases, including inflammation, proliferation, re-epithelialization, and remodeling. Delayed foot wound healing is a significant complication attributed to hyperglycemia in type 2 diabetes mellitus (DM) patients, and these wounds may develop into foot ulcers. Studies have shown that diabetic wounds heal less than 50% compared to non-diabetic wounds 30 days after they have encountered the wounds.

Multiple factors are responsible for the delay in wound healing. These include impaired fibroblast proliferation and migration, hyperglycemia, and impaired keratinocyte proliferation and migration. Another major cause of impaired wound healing is a sub-optimal immune response, increased levels of reactive oxygen species, deregulated angiogenesis, and persistent bacterial colonization at the site of the wound. Dermal fibroblasts are associated with every stage of the wound healing including hemostasis, inflammation, proliferation, and remodeling. In addition, the mechanistic understanding of chronic wounds has been a significant challenge due to the lack of appropriate genetic mouse models. The present disclosure demonstrates the effect of fibroblasts in diabetes-induced ulcers and illustrates accelerated wound healing with fibroblasts and fibroblast-derived materials.

Methods and Materials

Figure 1B:
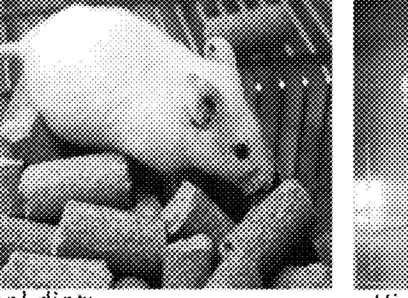
FIG. 1B shows attainment of desired baseline blood glucose levels over time.

Mice:

Polygenic model (Leptin gene, Leptin receptor (LEPR), $A^{y}$ gene mutation)-NONcNZO10/LtJ mice at 10-12 weeks from Jacksons Laboratory were used for the study. Mice were housed in individually vented cages on a 12-h light/dark cycle. Once the desired baseline blood glucose levels of 300 mg/dL were reached (FIG. 1), mice were placed on high-fat feeding (F3282 pellets) containing 36% fat (FIG. 1A).

Cell Culture:

Murine embryo Fibroblasts were obtained from American Type Culture Collection (ATCC®) and were cultured in DMEM High Glucose and supplemented with 10% Fetal bovine serum (FBS) and 1% penicillin-streptomycin, respectively. Cells were incubated at 37° C. in 5% $CO_2$.

Fibroblast-Derived Exosomes Isolation:

Conditioned Medium Preparation

Fibroblasts were plated and cultured in DMEM media with 10% FBS for 24 hours, then washed three times with PBS, and finally cultured in 3 ml serum-free DMEM media for 2 hours. The conditioned medium was collected and filtered through a 0.22-μm filter to remove cellular debris.

Isolation and Characterization of Exosomes Released by Fibroblasts

Exosomes were isolated from cultured fibroblasts by using Total Exosome Isolation Kit. In brief, 0.5 ml of total exosome isolation reagent was added to each 1 ml of filtered conditioned media and mixed well by inverting. After overnight incubation at 4° C., the mixture was centrifuged at 12,000×g for 70 min at 4° C., and all supernatant was removed by aspiration. Exosome pellets were resuspended in a very low volume of DMEM medium so as not to dilute prior to use.

In Vivo Treatment:

Cell Preparation Technique:

Cells will be cultured in T225 flasks at 37° C. Once the cells are 70% confluent, they are trypsinized with 0.5% trypsin and centrifuged at 400 g for 5 mins. The supernatant was discarded, and the pellets were resuspended in PBS. Cells PBS. $1\times10^6$ are aliquoted.

Full Thickness Wound Model:

Mice were anesthetized using inhalation of Isoflurane. Mice were shaved and sterilized with betadine and alcohol. On day 0, 4 full-thickness wounds were created using a sterile 8-mm punch biopsy on the back on either side of the midline at the level of the shoulders. Using serrated forceps, the skin was lifted, and a full-thickness wound through the subcutaneous tissue was created using an iris scissors.

Figure 2:
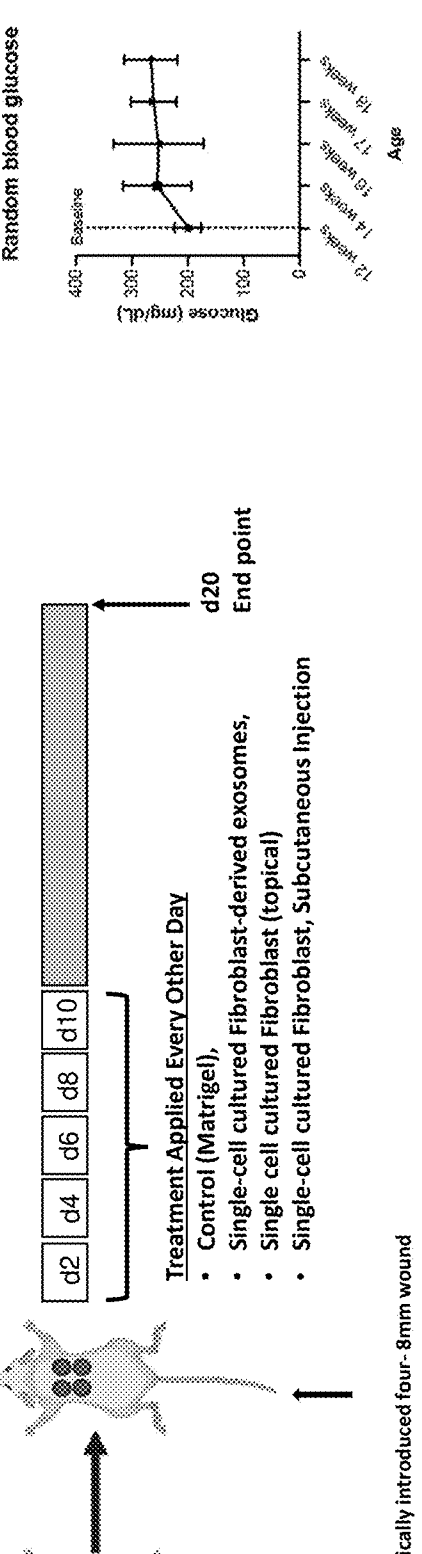
FIG. 2 provides one example of a regiment of wound treatment.

Wound Treatment:

Mice were anesthetized using inhalation of Isoflurane. Mice are grouped into four treatment groups: Matrigel, topical fibroblast (FB (Top)), fibroblast given subcutaneously (FB (SC)), and fibroblast-derived exosomes (FB-derived exosomes). The respective therapeutic compounds are gently smeared on the wound or subcutaneously administered around the wound. All mice received a total of 5 treatments (Day 1, Day 3, Day 5, Day 7, Day 9) (FIG. 2).

Wound Measurement:

The wounds were measured every day. Mice were anesthetized using 5% inhalation of Isoflurane. The wound diameter and area of the wound was measured using an eKare® insight advanced wound imaging device which is also approved for use in the clinic. After measurement, a clean occlusive dressing is re-applied, and the animal is kept warm until fully recovered. The wound closure for the four wounds was averaged per mouse.

Histology

Skin fragments encompassing the wounded area were excised and utilized for further analysis. For H&E staining, tissue samples are collected on Day 20 and fixed in 10% NBF, and embedded in paraffin. H&E staining was performed with ST Infinity H&E staining system, and Sirius red staining was performed with 0.1% picrosirius red. H&E-stained slides were imaged.

Immunolabeling of Tissues

For immunofluorescence with CD31, tissues were formalin-fixed and paraffin-embedded. Five-micrometer sections were rehydrated, and antigen retrieval was performed in 10 mM citrate buffer (pH 6.0) for 15 minutes to 1 hour. After one hour of blocking with 1% BSA at room temperature, the sections were incubated overnight at 4° C. with primary antibody (CD31, Thermo Fisher) and then with secondary antibody (Alexa Fluor 568, goat, anti-rat, Thermo-Fisher) for 1 hour at room temperature.

For paraffin-embedded samples, tissues were fixed in 4% buffered paraformaldehyde (PFA) for 20 min and permeabilized in 0.3% Triton-X for 30 min. After blocking with 1% BSA (30 min at room temperature), the sections were incubated overnight at 4° C. with primary antibody (Cytokeratin 5, Thermo Fisher), followed by secondary antibodies (Alexa Fluor 546, goat anti-rabbit) for 1 hour at room temperature, and 30-min incubation with nuclear stain (DAPI).

Quantitative Real-Time PCR

RNA was isolated from snap-frozen tissues and extracted with Trizol reagent according to the manufacturer's instructions. cDNA was synthesized using a High-Capacity cDNA Reverse Transcription Kit. Real-time quantitative PCR was carried out using SYBR Green Real-Time PCR Master Mix.

Enzyme-Linked Immunosorbent Assay

Collection of Serum:

Blood was allowed to clot for 2 hours at room temperature before centrifuging for 15 mins at 2000 g to separate the serum and begin the assay immediately.

Tissue biopsy samples. Biopsy samples of healing wound areas were taken at several time points during the experiment, flash frozen, and stored. Lysates from these tissues were then used to assay for cytokines and growth factors.

Mouse Cytokine Array Analysis:

Mouse cytokine antibody arrays were performed using the Abcam Mouse cytokine antibody array (120 targets—ab197461) kit according to the manufacturer's instructions.

List of Cytokines Detected in the Array Analysis:

Tumor necrosis factor (TNF-α),
interleukin-6 (IL-6),
IL-1,
interferon-gamma (IFN-γ),
IL10;
epidermal growth factor (EGF),
vascular endothelial growth factor (VEGF).

Results

Topical Fibroblasts Accelerate Wound Healing in Diabetics

To demonstrate that topically administered fibroblasts accelerate wound healing, NONcNZO10/LtJ mice aged 10-12 weeks were administered a high-fat diet with 36% fat after their baseline blood glucose levels reached the desired 300 mg/dL concentration. Once the blood glucose levels reached 300 mg/dL, mice were randomized into four treatment groups: Matrigel, topical fibroblast (FB (Top)), fibroblast given subcutaneously (FB (SC)), and fibroblast-derived exosomes (FB-derived exosomes). Four 8 mm wounds were created at the back of each of these mice, and they were treated with 50 μL of their respective treatments mixed with Matrigel. The diameter of these wounds were measured every other day until the wounds healed, and the mice were euthanized for further analysis. Treatment effectiveness was assessed by plotting the wound diameter and area using the diameter and area data generated by eKare® insight advanced wound imaging device which is also approved for use in the clinic.

Figure 3:
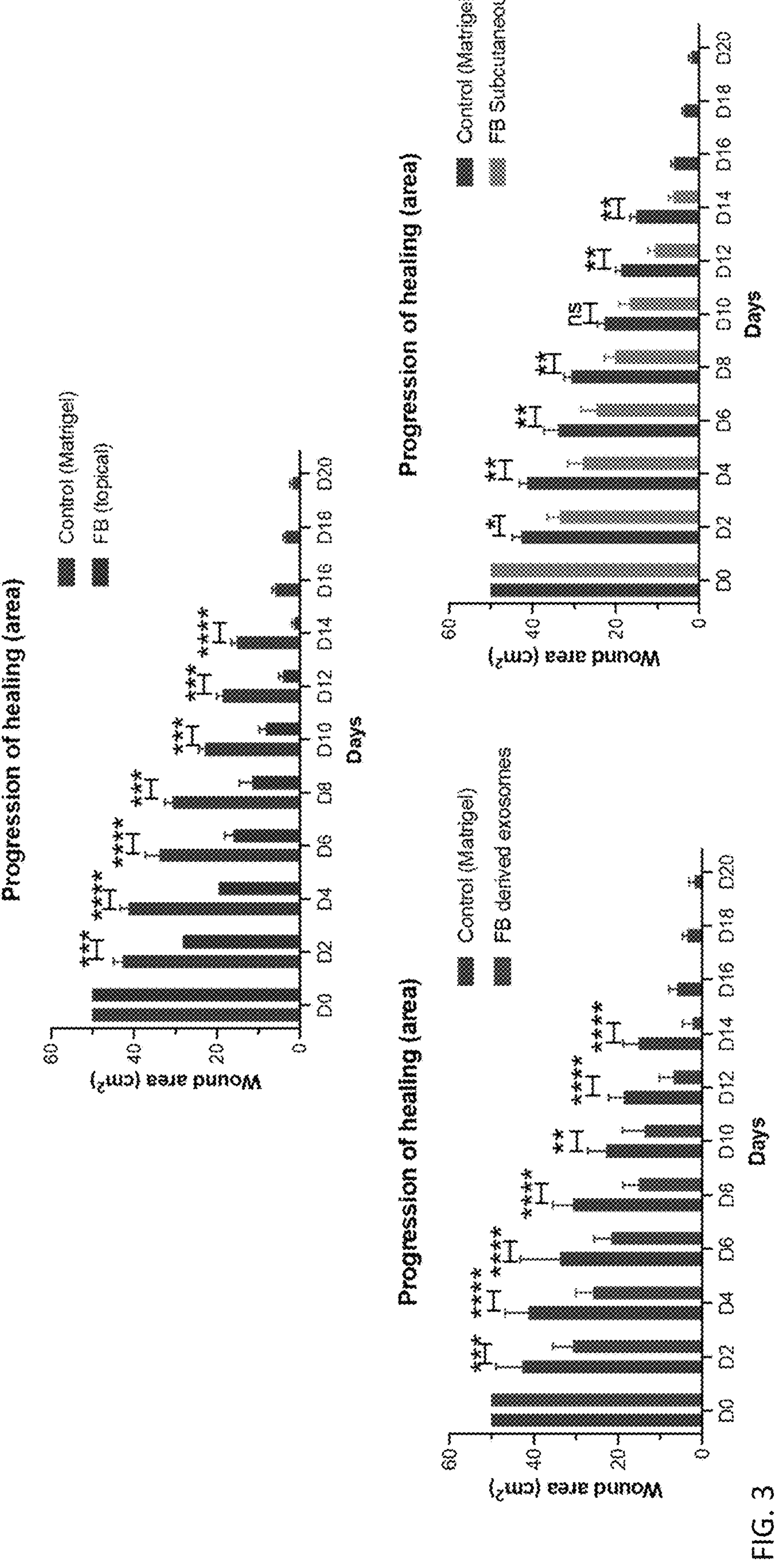
FIG. 3 demonstrates day-to-day wound closure progression when comparing control Matrigel with topically provided fibroblasts (FB) (top image where the control bar is left of the FB bar); control Matrigel compared to FB-derived exosomes (bottom left image where the control bar is left of the FB bar); and control Matrigel compared to subcutaneously provided FB (bottom right image where the control bar is to the left of the FB bar).
Figure 4:
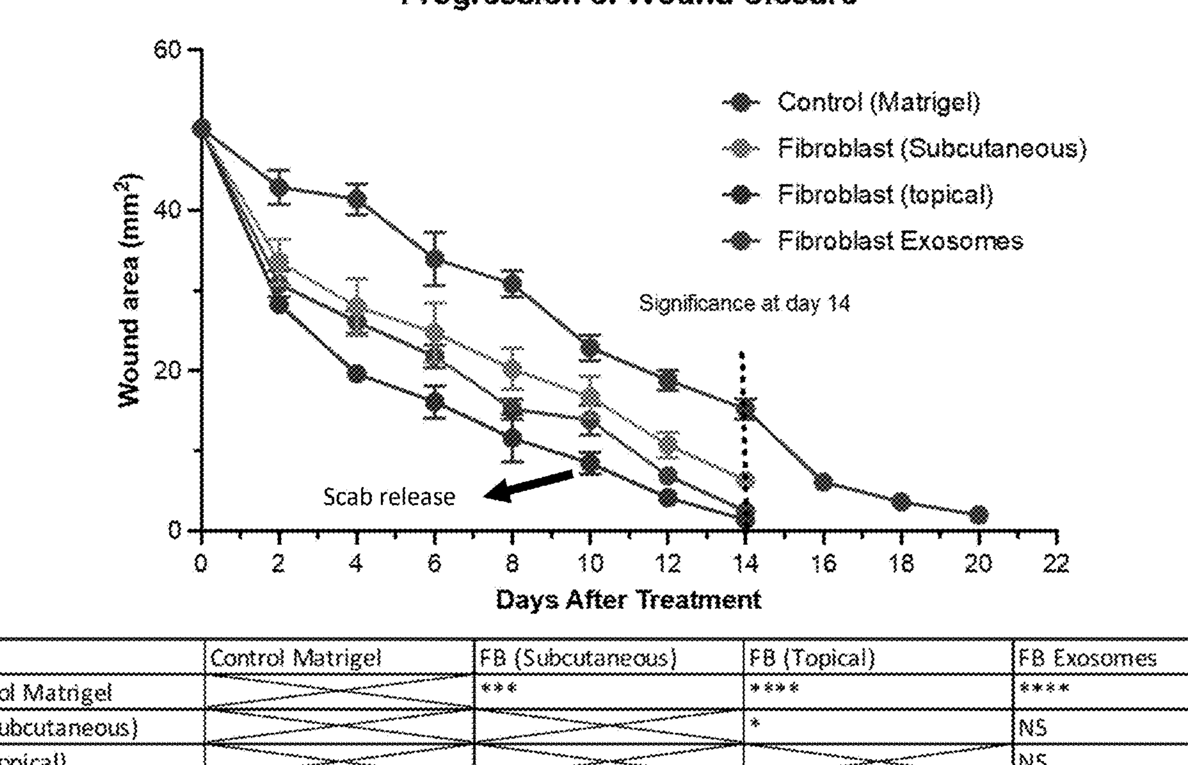
FIG. 4 shows progression of wound closure comparing control Matrigel (top line) with subcutaneously provided fibroblasts (second line from the top), fibroblast exosomes (third line from the top), and topically provided fibroblasts (bottom line).
Figure 5:
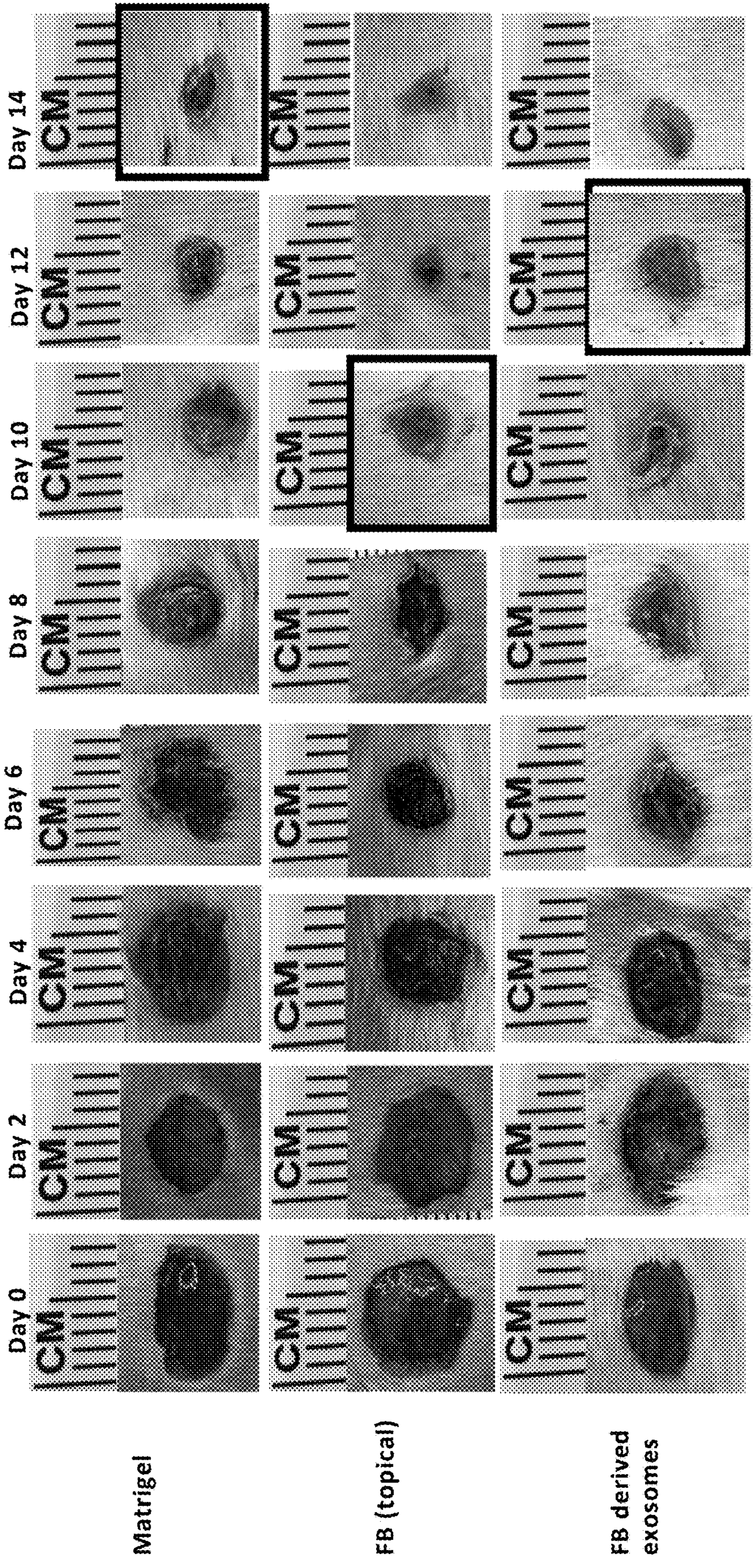
FIG. 5 shows representative images of wound healing and closure.
Figure 6:
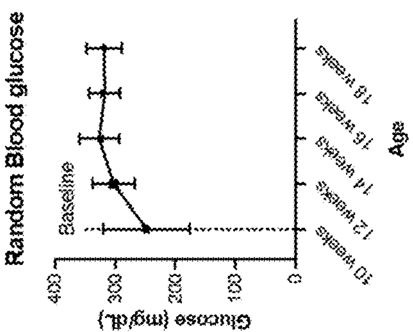
FIG. 6 shows one example of an experiment design to examine the effects of freeze/thaw storage on fibroblast exosomes and fibroblast lysate.
Figure 6:
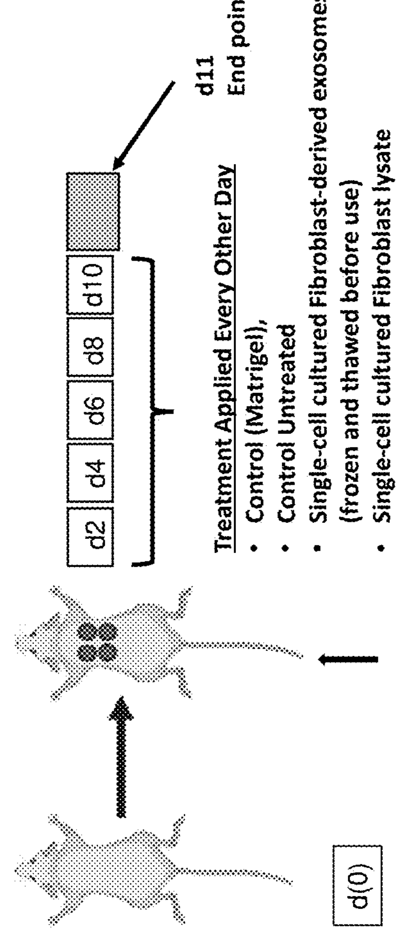
Figure 7:
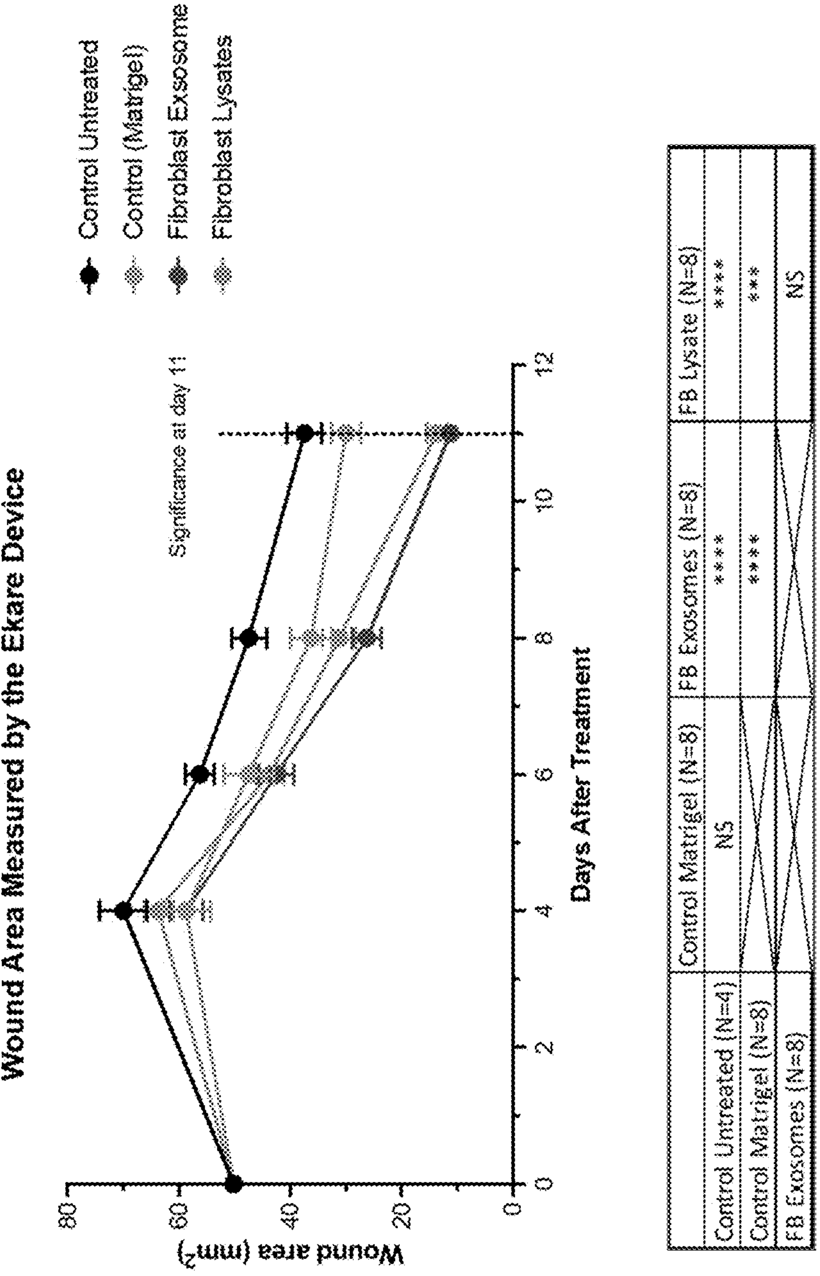
FIG. 7 demonstrates the impact of frozen/thawed fibroblast exosomes and fibroblast lysate.
Figure 8:
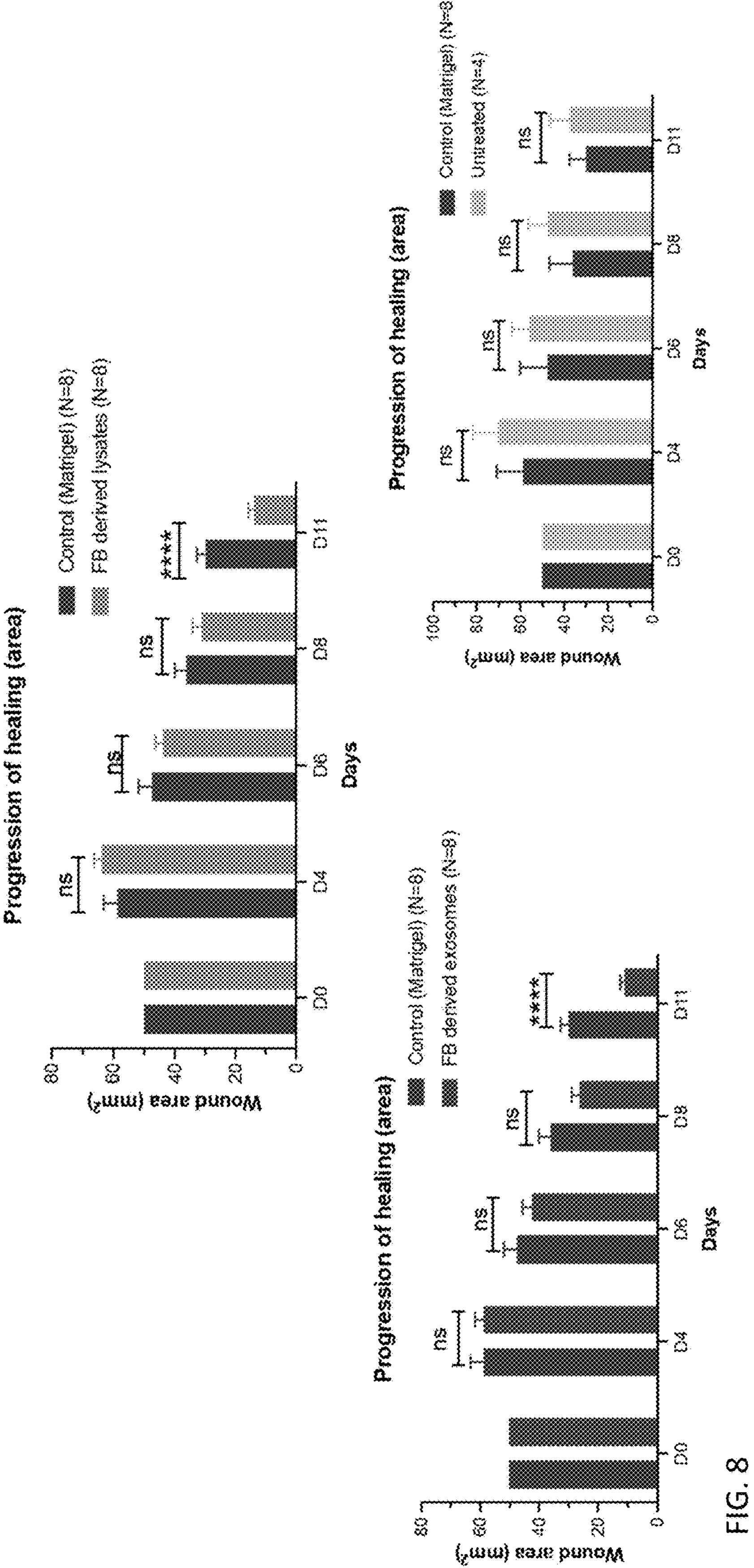
FIG. 8 demonstrates day-to-day wound closure progression :freeze/thaw embodiments.
Figure 9:
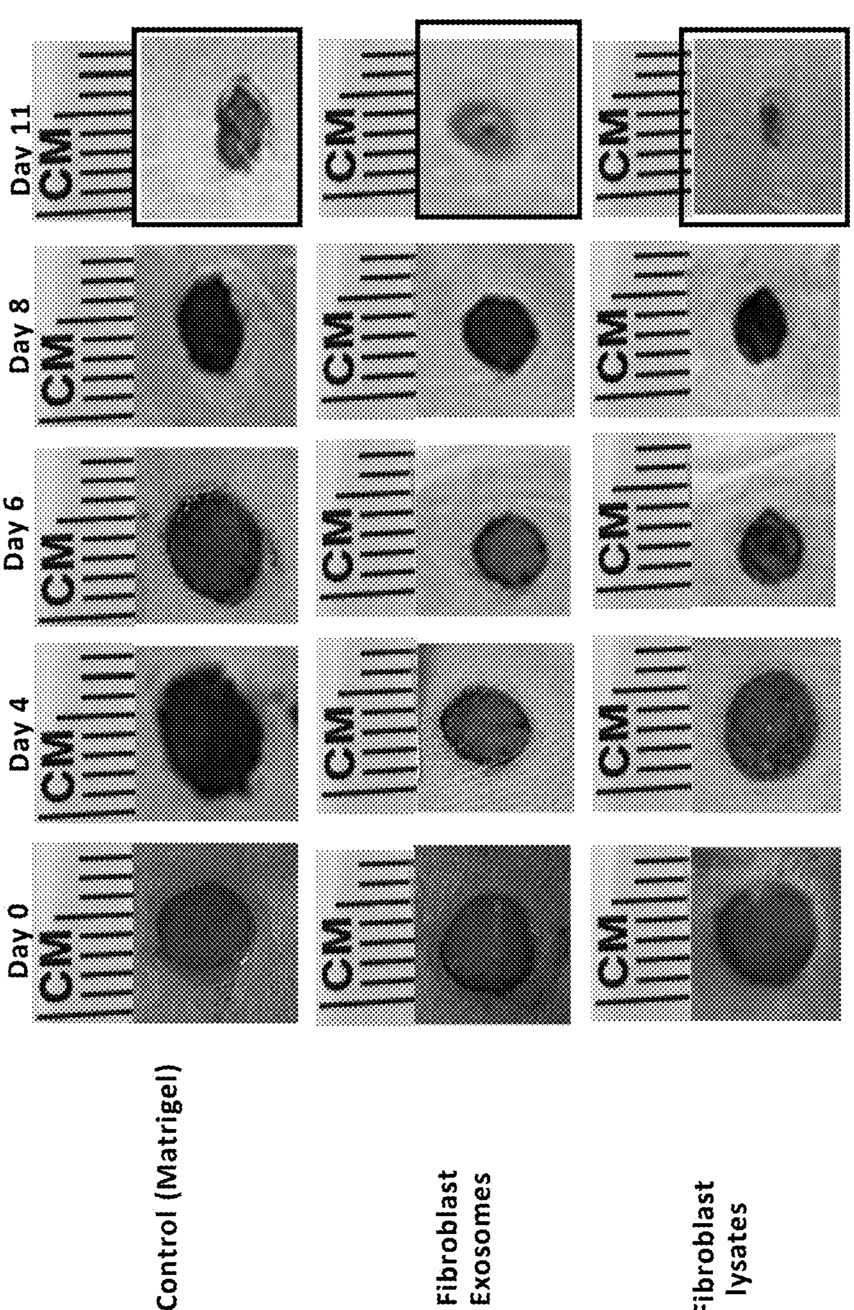
FIG. 9 shows wound closure with fibroblast and fibroblast-derived exosomes.

The experiment and the analysis of the captured data confirmed that mice treated with FB (topical) showed an accelerated wound healing rate compared to the control group that received Matrigel only. (FIG. 3) Wound area measurement also revealed a significant improvement in wound size in the mice that received FB (topical), followed by FB-derived exosomes and FB (SC), compared to the control groups. This finding also confirmed that FB (topical) accelerates wound healing in diabetic wounds, followed by fibroblast-derived exosomes.

Significance of Certain Embodiments

In this study, it is demonstrated that topically administered fibroblasts show a significant increase in the rate of wound healing when compared to the controls. There also seems to be a substantial and significant improvement in mice that received fibroblast-derived exosomes. These results suggest that the direct application of fibroblasts and fibroblast-derived material and their migration and proliferation at the dermal layer accelerates the wound healing rate in diabetic wounds. Passive accumulation of fibroblasts at the wound site, and their well-established role in immune modulation, trigger an immune response that regulates angiogenesis and accelerates the wound healing rate. Fibroblast and fibroblast-derived material increase the healing rate, and the immune modulation of fibroblasts also prevents bacterial colonization, a known factor for delayed healing in diabetic wounds. These findings are a critical validation step in increasing the therapeutic efficacy of a fibroblast treatment modality.

CONCLUSION

The continued testing of several treatment modalities for the delivery of fibroblasts and fibroblast-derived materials to the wound site resulted in a significant improvement in healing rates with topically applied fibroblasts and with fibroblast-derived exosomes. The finding addresses the major issue that exists in diabetic wound healing and is useful to cure this chronic disease associated with diabetics.

Example 2

Wound Care

In one in vivo study, the inventors tested single cell fibroblast administration on a wound generated in a diabetic mouse model. One million single cell fibroblasts were either administered topically or subcutaneously around the wound edges. Fibroblast exosomes derived from one million fibroblast media used to grow the single cell fibroblasts were also tested for topical administration. The topical cells and exosomes were mixed with Matrigel® just prior to application so as to keep the cells and the exosomes on the wound. As control, Matrigel® alone was utilized. All control and test samples were administered every other day after measuring the wound diameter and area. The wounds were considered healed once the scab was released from the wound, and epithelialization was visible (FIGS. 2-7).

The results of this study indicated that single cell fibroblasts administered topically, and subcutaneously, as well as fibroblast-derived exosomes, healed the wound significantly faster than the control. In this study, of the three test materials, single cell fibroblasts, and fibroblast-derived exosomes performed significantly better than the subcutaneously-injected fibroblasts.

In another study, the purpose of an in vivo experiment was to test the efficacy of single cell fibroblasts, and fibroblast-derived exosomes that have been previously frozen (e.g., in liquid nitrogen) and then thawed just before use. One million single cell fibroblasts were administered topically. Fibroblast exosomes derived from one million fibroblast media used to grow the single cell fibroblasts were also tested for topical administration. The topical cells and exosomes were mixed with Matrigel® just prior to application so as to keep the cells and the exosomes on the wound. As control, Matrigel® alone was utilized. All control and test samples were administered every other day after measuring the wound diameter and area. Wound size was determined every other day using the eKare® device that is clinically approved for use in monitoring chronic wound healing. The eKare® device also takes images of the wounds. The wounds were considered healed once the scab was released from the wound, and epithelialization was visible (see FIGS. 6-9).

The results of this study indicated that frozen/thawed single cell fibroblasts administered topically, as well as the frozen-thawed fibroblast-derived exosomes, healed the wound significantly faster than the control. This study indicated that freeze/thawing of the cells or the exosomes did not impact the efficacy of the materials on wound healing.

In another study, the purpose was to test an alternative, easier method of covering the wounds after fibroblast cell, or fibroblast-derived exosomes, were topically administrated on the wound. Matrigel is an animal product that is not presently approved for human use, so other products that have been approved for use as a wound cover on humans were utilized. For the study, the inventors tested 3M Nexcare® and ElaSkin® by applying the wound cover material in the surface of a culture place, and then inoculating the plate with fibroblast cells and monitoring the growth of the cells in terms of number, as well as cell size, using an instrument called IncuCyte® from Agilent Inc.

Figure 10:
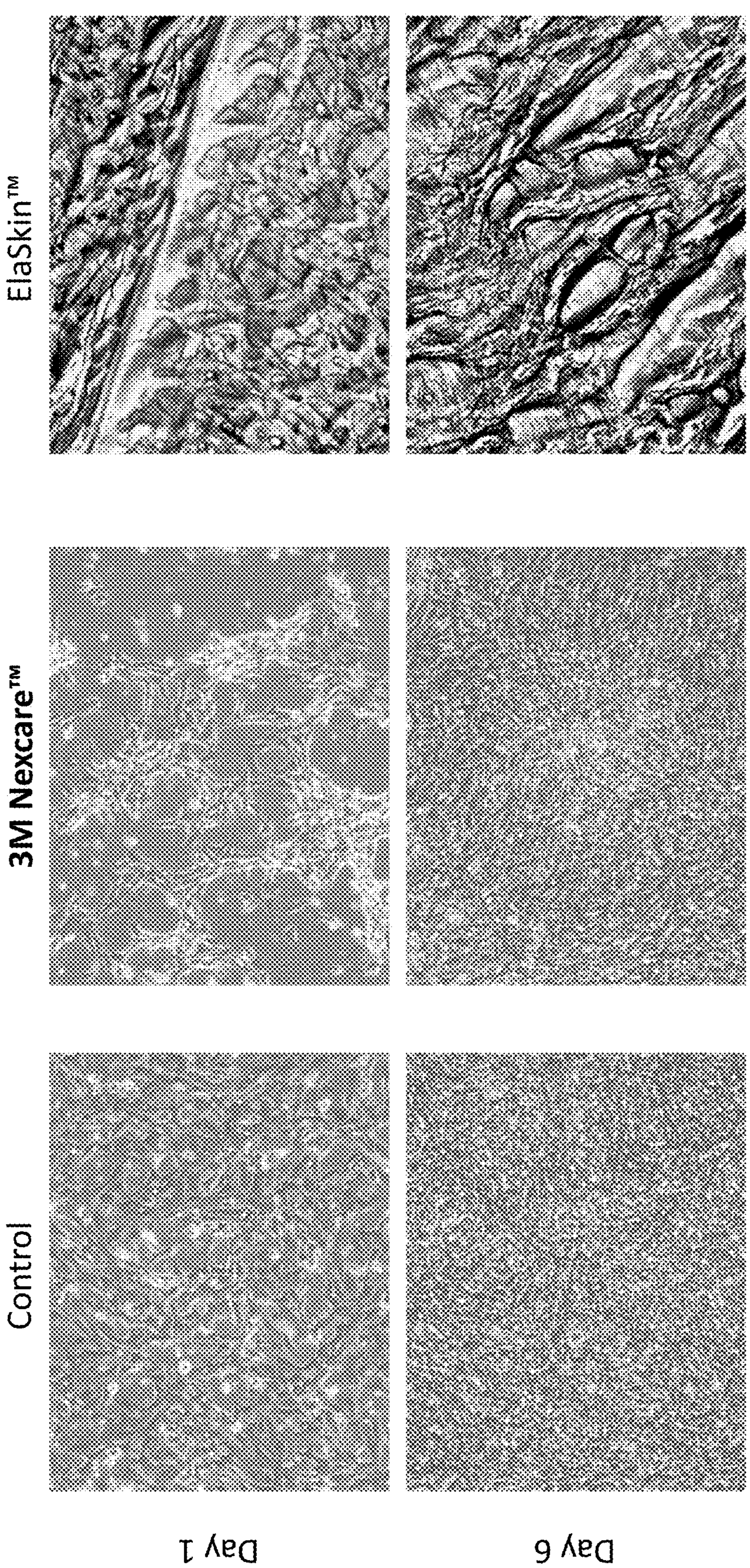
FIG. 10 shows an example of a test of wound cover products on cell viability, particularly a test of 3M Nexcare® and ElaSkin® on mouse dermal fibroblast cells.
Figure 11:
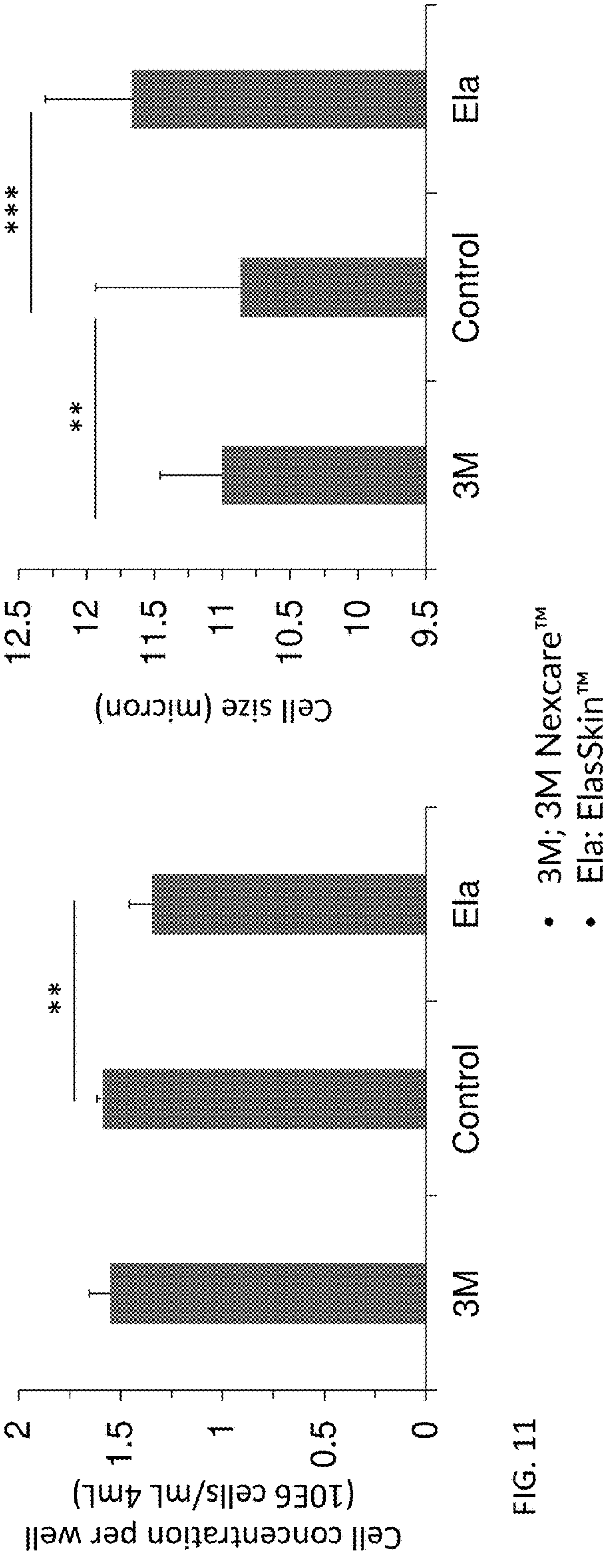
FIG. 11 shows the impact of growth and cell size as compared to control untreated cells.

The results of the study indicated that 3M Nexcare® did not impact the growth efficiency or size of the cells, whereas ElaSkin® had a significant impact not only on the growth of the cells, but also on the cell size, indicating adverse impact on cell growth. As a result of this study, 3M Nexcare® was utilized in subsequent studies to cover the fibroblast cells and fibroblast-derived exosomes on the wounds (FIGS. 10-11).

Figure 12:
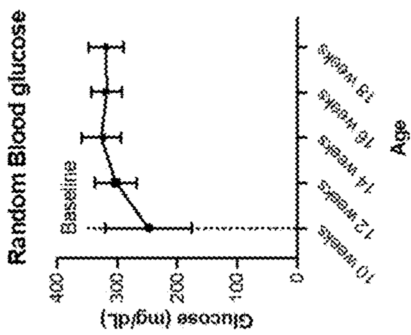
FIG. 12 provides one example of a study design to examine the effects of fibroblast spheroids on wound healing covered with 3M Nexcare®.
Figure 12:
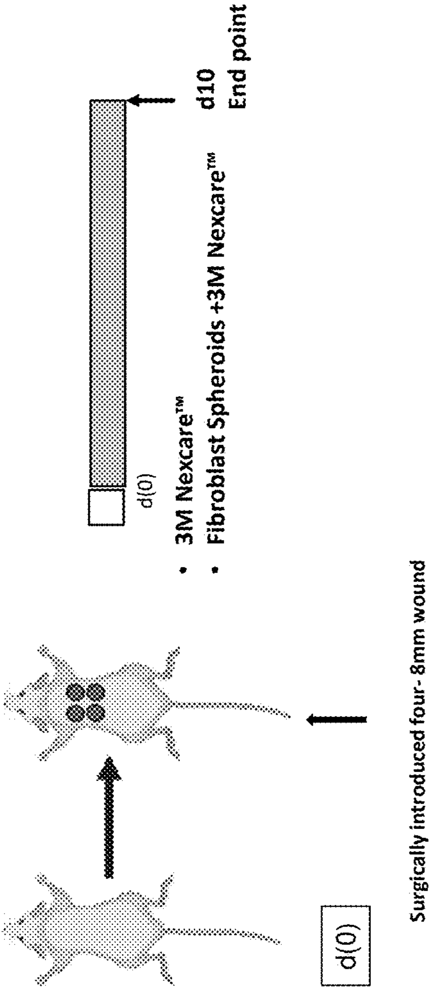
Figure 13:
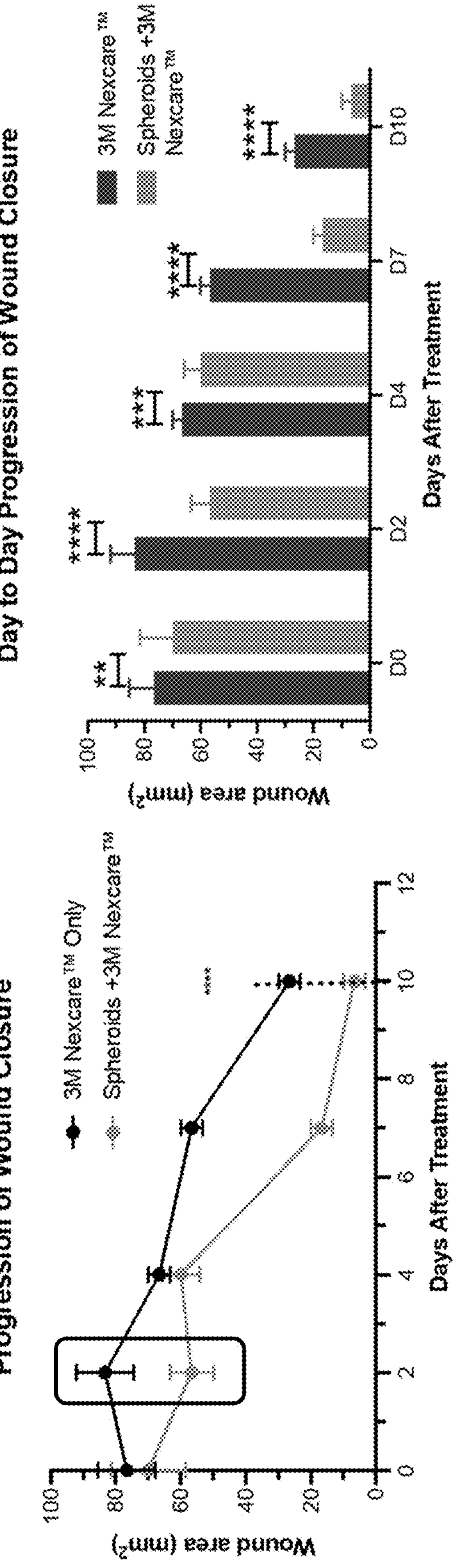
FIG. 13 demonstrates fibroblast spheroids tested with 3M Nexcare® wound cover. In the left image, the Spheroids+3M Nexcare® line is the bottom line. On the right image, the Spheroids+3M Nexcare® bar is left of the 3M Nexcare® control bar.
Figure 14:
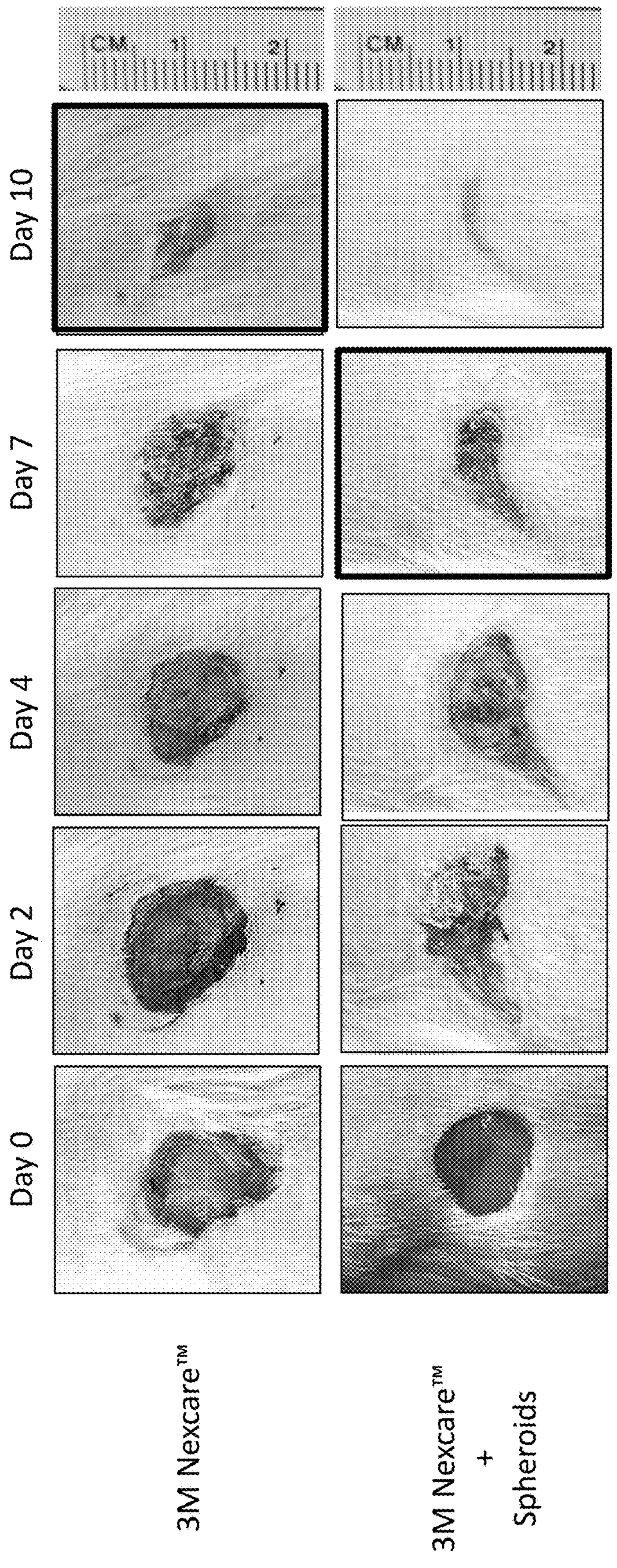
FIG. 14 provides representative images of wound healing with spheroids covered with 3M Nexcare™.
Figure 15:
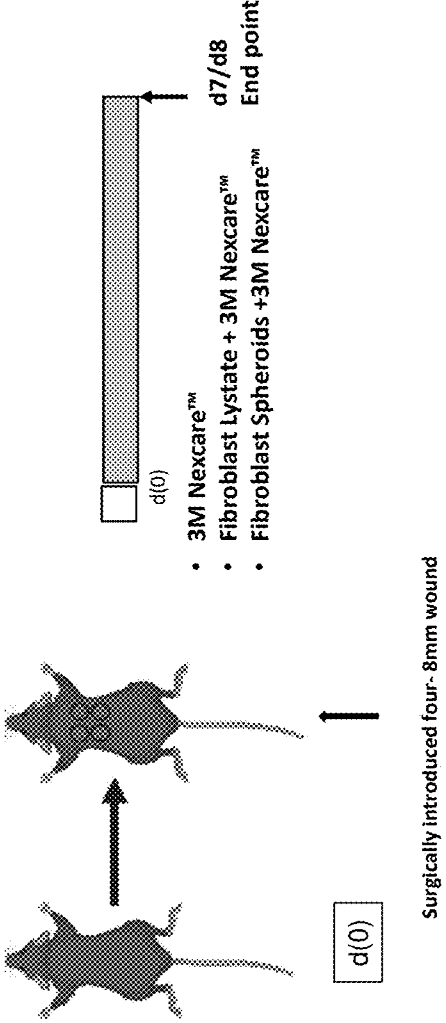
FIG. 15 provides one example of a study design to examine the effects of fibroblast spheroids and lysate on wound healing in wild type mice.
Figure 16:
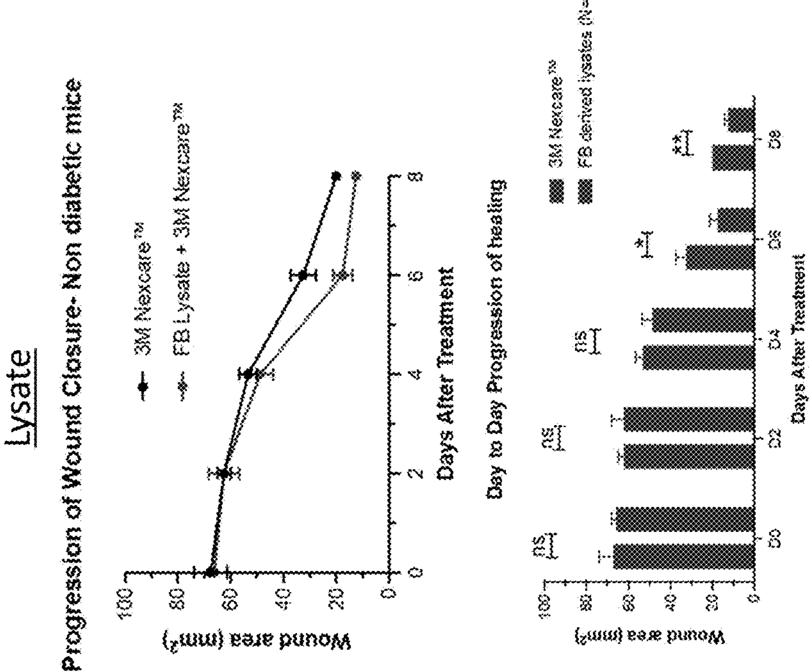
FIG. 16 demonstrates the effect of spheroids and lysate with 3M Nexcare® on wild type mice. In the top left image, Spheroids+3M Nexcare® is the lower line. In the bottom left image, the Spheroids+3M Nexcare® bar is to the right of the 3M Nexcare® bar. In the upper right image, the FB Lysate+3M Nexcare® line is below the 3M Nexcare® line. In the bottom right image, the FB derived lysates+3M Nexcare® bar is to the right of the control 3M Nexcare® bar.
Figure 16:
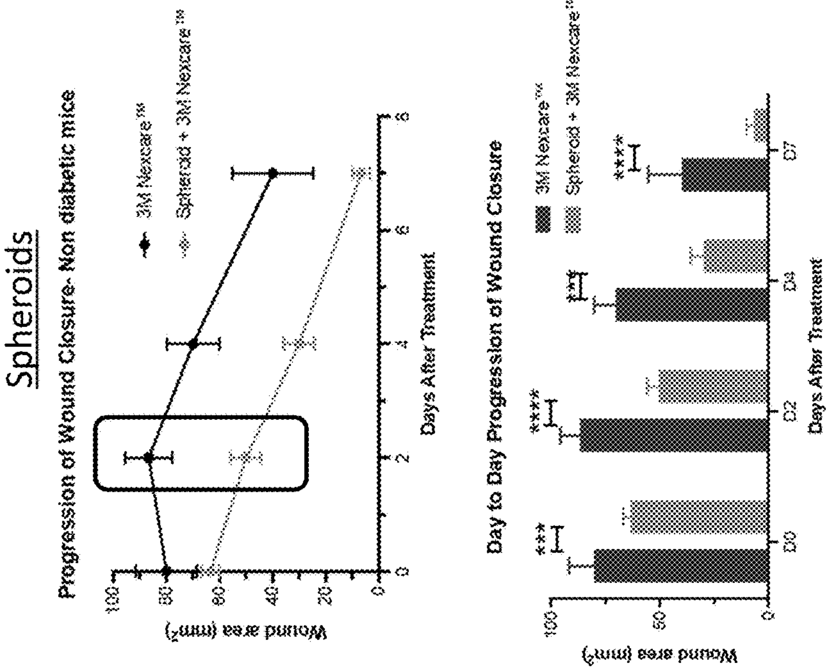
Figure 17:
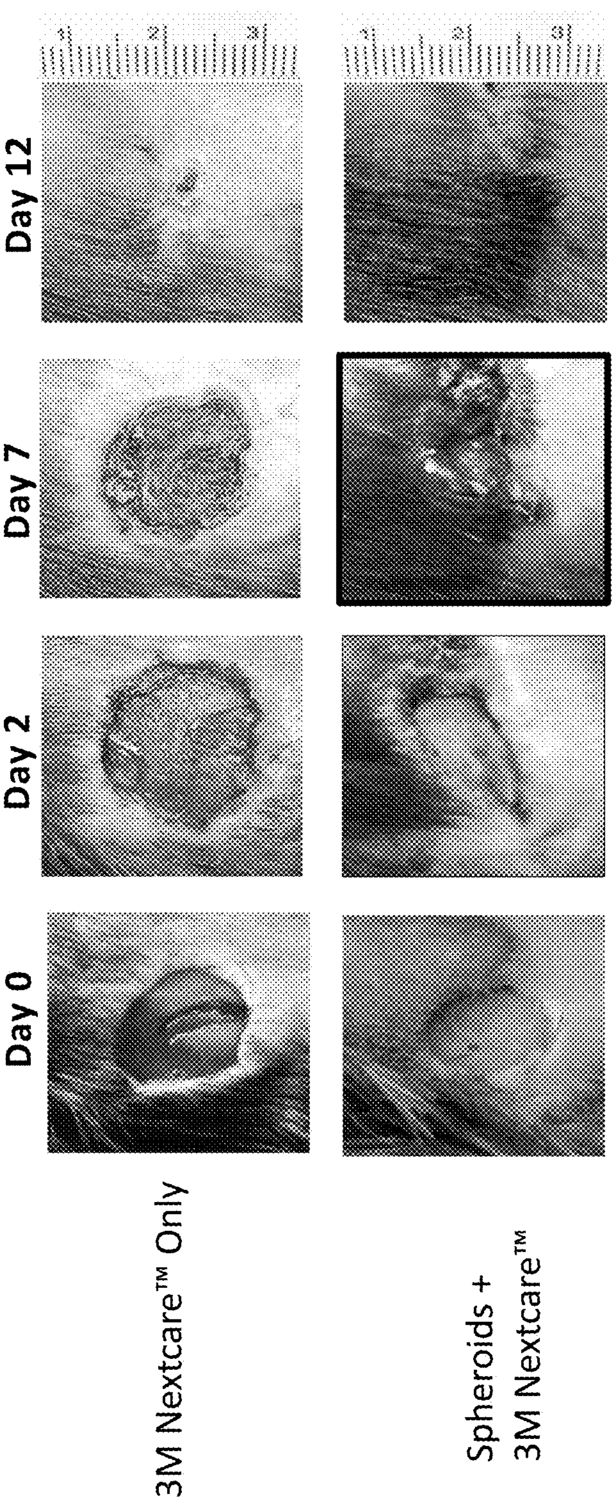
FIG. 17 provides images for fibroblast spheroids with 3M Nexcare® cover vs. 3M Nexcare® cover only in wild type mice.
Figure 18:
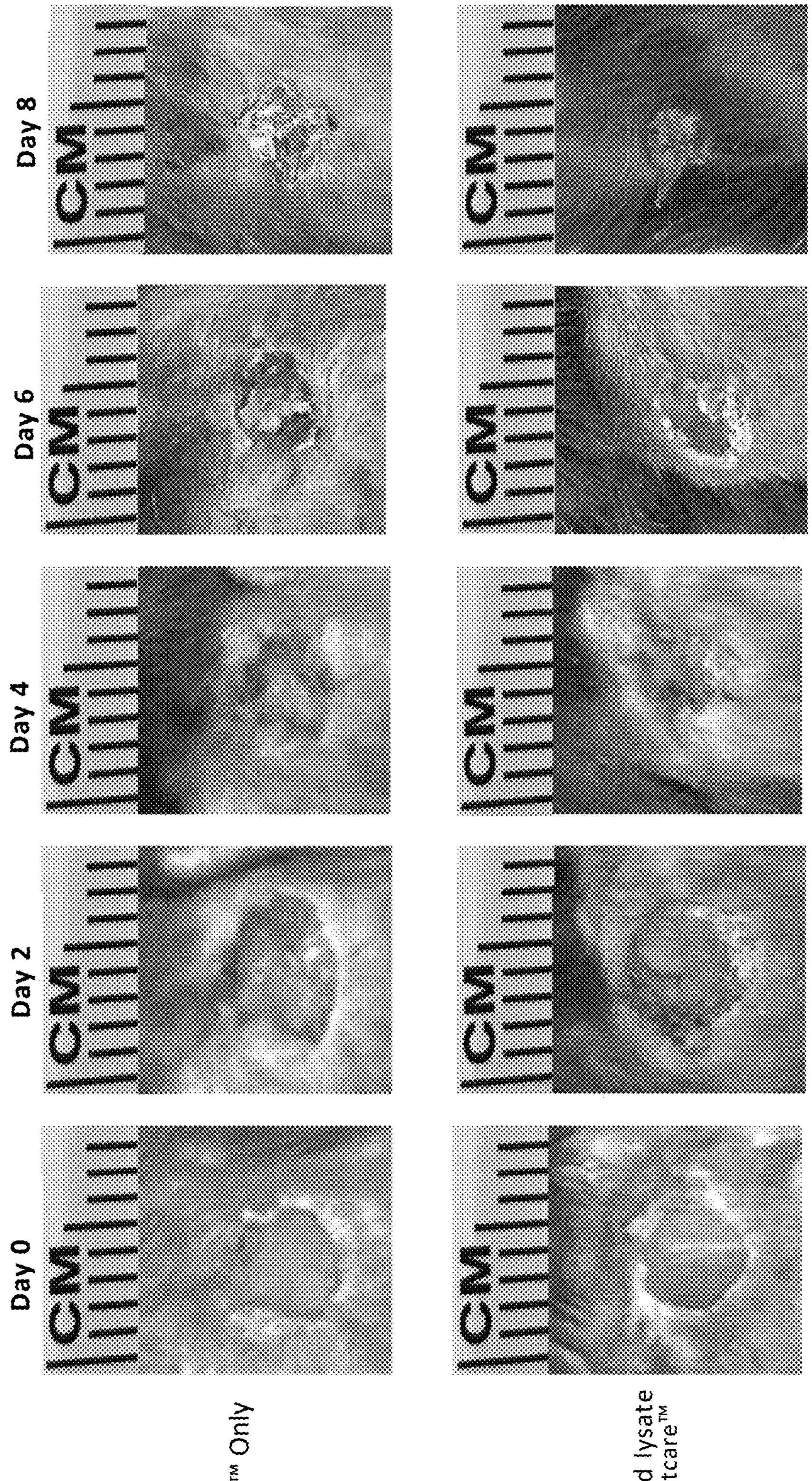
FIG. 18 provides representative images showing the effect of fibroblast lysate on wild-type mouse wound closure with 3M Nexcare® cover.
Figure 19:
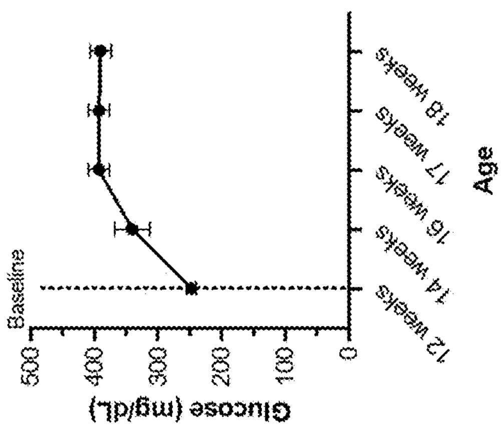
FIG. 19 provides one example of a study design to examine the effects of one-time treatment with mouse fibroblast spheroids, human fibroblast spheroids+3M Nexcare®, compared with Grafix®.
Figure 19:
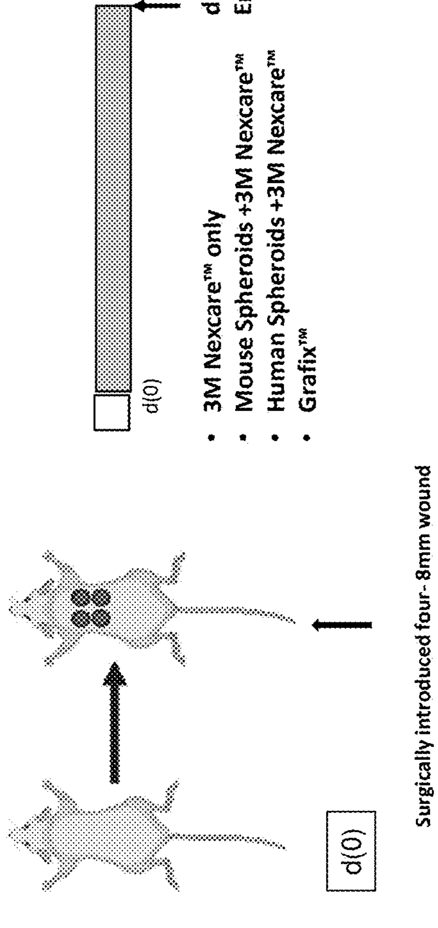
Figure 20:
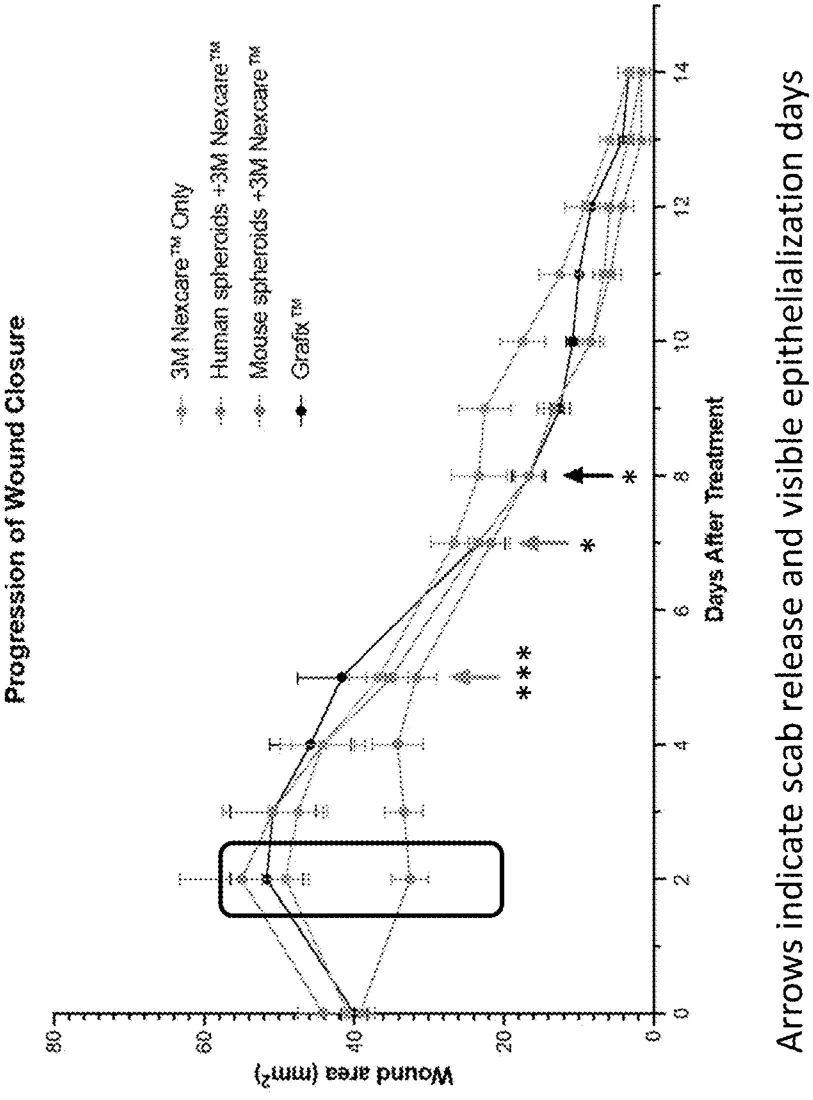
FIG. 20 provides mouse and human fibroblast spheroids wound healing progression comparison with Grafix® in diabetic mice.
Figure 21:
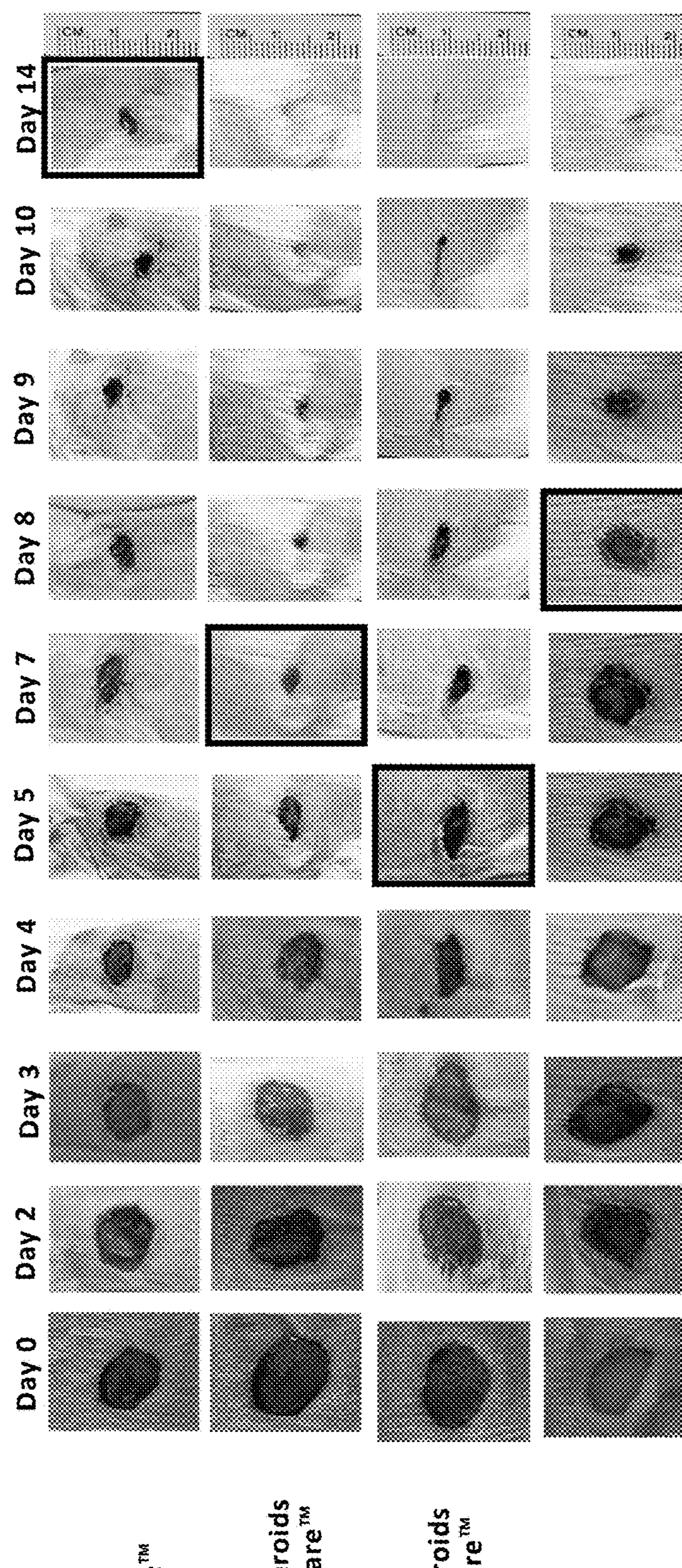
FIG. 21 provides representative images of wound closure with fibroblast spheroids compared to Grafix®.
Figure 22:
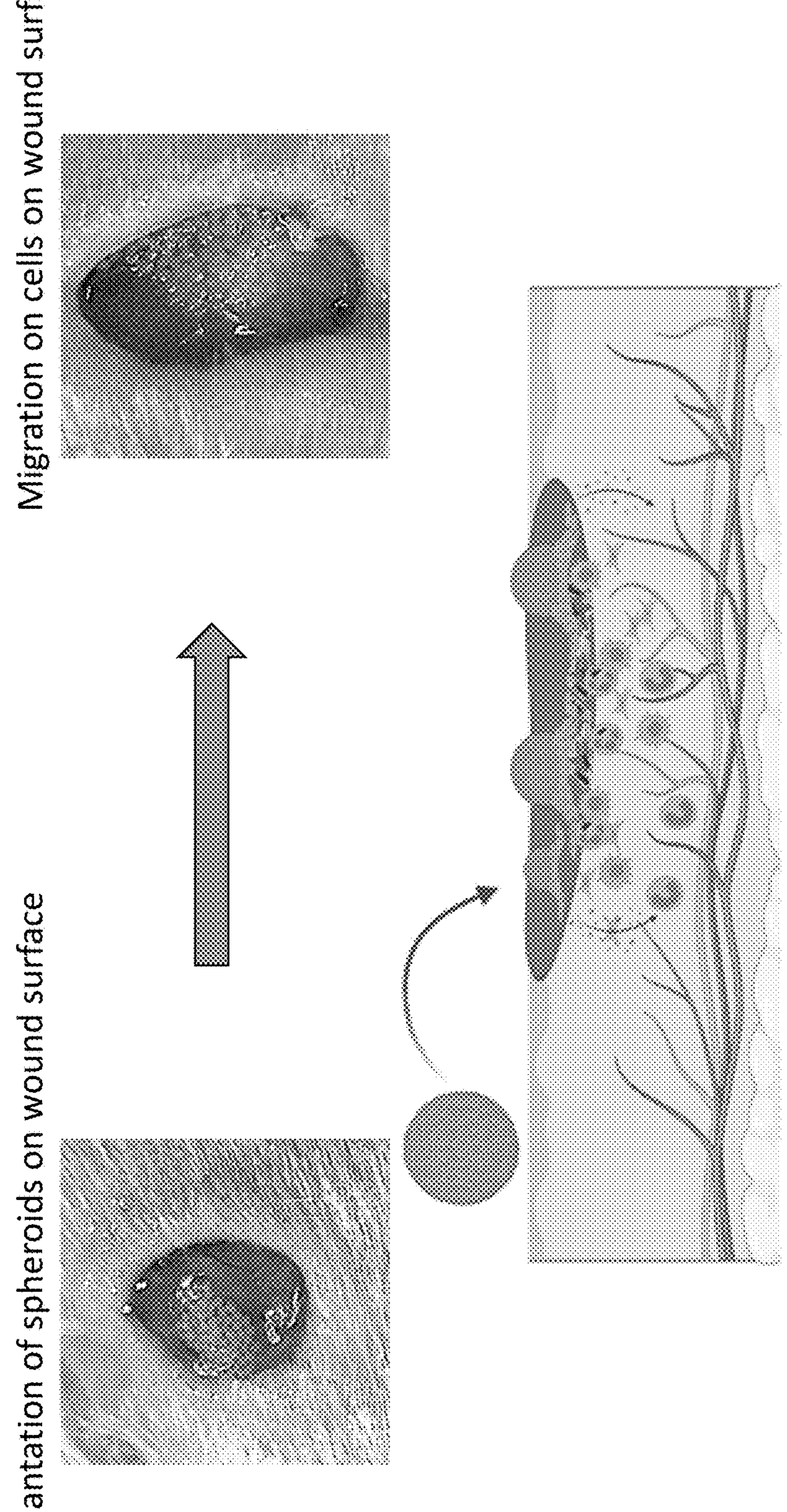
FIG. 22 shows an example of fibroblast spheroids implantation, migration, and proliferation on wound surface.

In an additional study, the purpose of the in vivo experiment was to test fibroblast cells grown as a spheroid organoid and its administration on a wound generated in a diabetic mouse model. One hundred fibroblast spheroids, with each spheroid containing approximately 30,000 fibroblast cells (plus or minus of up to 15%), were administered topically on the wound. The wounds were then covered by applying 30-50 μl of 3M Nexcare® on the wound. As control only 3M Nexcare® was utilized. The spheroids and control samples were only applied once to be able to test a one-time application of the spheroid fibroblasts. Wound size was determined every other day using the eKare® device that is clinically approved for use in monitoring chronic wound healing. The eKare® device also takes images of the wounds. The wounds were considered healed once the scab was released from the wound, and epithelialization was visible (FIGS. 12-14).

The results of this experiment indicated that spheroid fibroblasts administered healed the wound significantly faster than the control. Not only did the wounds heal approximately three days faster than control, the inflammation of the wound treated with fibroblasts was significantly less than the control.

In one study, the purpose of the in vivo experiment was to test fibroblast cells grown as a spheroid organoid, as well as single cell fibroblast-derived lysate and its administration on a wound generated in a wild-type non-diabetic mouse model. One hundred fibroblast spheroids, with each spheroid containing approximately 30,000 fibroblast cells (plus or minus of up to 15%) were administered topically on the wound. Also tested on the wounds was lysate derived from mechanically lysing 1 million single cell fibroblasts. The wounds were then covered by applying 30-50 μl of 3M Nexcare® on the wound. As control, the inventors tested only 3M Nexcare®. The spheroids, fibroblast lysate, and control samples were only applied once to test a one-time application of the spheroid fibroblasts, and lysate. Wound size was determined every other day using the eKare® device that is clinically approved for use in monitoring chronic wound healing. The eKare® device also takes images of the wounds. The wounds were considered healed once the scab was released from the wound, and epithelialization was visible (FIGS. 17-20).

The results of this study indicated that spheroid fibroblasts, as well as the fibroblast-derived lysate, healed the wound significantly faster than the control even in non-diabetic wounds. When comparing the fibroblasts spheroids to the lysate, the fibroblast spheroids healed with wound significantly faster than the lysate.

In another study, the purpose of the in vivo study was to test administration on a wound generated in a diabetic mouse model both mouse dermal fibroblasts and human dermal fibroblast cells grown as spheroid organoids. Additionally, the inventors wanted to test a commercially available product called Grafix® which is FDA approved for use in treating chronic wounds. One hundred fibroblast spheroids, with each spheroid containing approximately 30,000 (plus or minus up to 15%) fibroblast cells, were administered topically on the wound. The inventors also tested Grafix® on the wounds by following the direction of application provided in publications for Grafix®. The wounds were then covered by applying 30-50 μl of 3M Nexcare® on the wound. As control, the inventors tested only 3M Nexcare®. The human and mouse fibroblast spheroids, Grafix®, and control samples were only applied once to test a one-time application of the spheroid fibroblasts and Grafix®. Wound size was determined every other day using the eKare® device that is clinically approved for use in monitoring chronic wound healing. The eKare® device also takes images of the wounds. The wounds were considered healed once the scab was released from the wound, and epithelialization was visible (FIGS. 21-24).

The results of this study indicated that human dermal spheroid fibroblasts healed the wound significantly faster than the control, mouse dermal fibroblast spheroids, and the Grafix®. The wounds healed at day 5 with the human dermal fibroblast spheroids, at day 7 with the mouse dermal fibroblast spheroids, and at day 8 with Grafix®. The human dermal fibroblast spheroids also controlled the inflammation significantly better than the other test materials by not seeing an increase in wound size after administration. In fact, there was an immediate reduction in wound size after administration of the human dermal fibroblasts. When comparing the human dermal fibroblasts spheroids to the mouse dermal fibroblast spheroid, the fibroblast spheroids healed the wound significantly faster.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Chuong, C. M., et al., What is the 'true' function of skin? Exp Dermatol, 2002. 11(2): p. 159-87.
2. Bainbridge, P., Wound healing and the role of fibroblasts. J Wound Care, 2013. 22(8): p. 407-8, 410-12.
3. Tracy, L. E., R. A. Minasian, and E. J. Caterson, Extracellular Matrix and Dermal Fibroblast Function in the Healing Wound. Adv Wound Care (New Rochelle), 2016. 5(3): p. 119-136.
4. Darby, I. A. and T. D. Hewitson, Fibroblast differentiation in wound healing and fibrosis. Int Rev Cytol, 2007. 257: p. 143-79.
5. Shah, J. M., et al., Cellular events and biomarkers of wound healing. Indian J Plast Surg, 2012. 45(2): p. 220-8.
6. Darby, I. A., et al., Fibroblasts and myofibroblasts in wound healing. Clin Cosmet Investig Dermatol, 2014. 7: p. 301-11.
7. Schultz, G. S. and A. Wysocki, Interactions between extracellular matrix and growth factors in wound healing. Wound Repair Regen, 2009. 17(2): p. 153-62.
8. Huang, Y. Z., et al., Mesenchymal Stem Cells for Chronic Wound Healing: Current Status of Preclinical and Clinical Studies. Tissue Eng Part B Rev, 2020. 26(6): p. 555-570.
9. Farahani, M. and A. Shafiee, Wound Healing: From Passive to Smart Dressings. Adv Healthc Mater, 2021. 10(16): p. e2100477.
10. Barrientos, S., et al., Growth factors and cytokines in wound healing. Wound Repair Regen, 2008. 16(5): p. 585-601.
11. Fathollah S, Mirpour S, Mansouri P, Dehpour A R, Ghoranneviss M, Rahimi N, Safaie Naraghi Z, Chalangari R, Chalangari K M. Investigation on the effects of the atmospheric pressure plasma on wound healing in diabetic rats. Sci Rep. 2016 Feb. 23; 6:19144. doi: 10.1038/srep19144. PMID: 26902681; PMCID: PMC4763329.
12. Burgess J L, Wyant W A, Abdo Abujamra B, Kirsner R S, Jozic I. Diabetic Wound-Healing Science. Medicina (Kaunas). 2021 Oct. 8; 57(10):1072. doi: 10.3390/medicina57101072. PMID: 34684109; PMCID: PMC8539411.
13. Patel S, Srivastava S, Singh M R, Singh D. Mechanistic insight into diabetic wounds: Pathogenesis, molecular targets and treatment strategies to pace wound healing. Biomed Pharmacother. 2019 April; 112:108615. doi: 10.1016/j.biopha.2019.108615. Epub 2019 Feb. 20. PMID: 30784919.
14. Fang R C, Kryger Z B, Buck D W 2nd, De la Garza M, Galiano R D, Mustoe T A. Limitations of the db/db mouse in translational wound healing research: Is the NONcNZO10 polygenic mouse model superior? Wound Repair Regen. 2010 November-December; 18(6):605-13. doi: 10.1111/j.1524-475X.2010.00634.x. Epub 2010 Oct. 18. PMID: 20955341.
15. Blaber S I, Diaz J, Blaber M. Accelerated healing in NONcNZO10/LtJ type 2 diabetic mice by FGF-1. Wound Repair Regen. 2015 July-August; 23(4):538-49. doi: 10.1111/wrr.12305. PMID: 25891187.

What is claimed is:

1. A method of treating one or more wounds in an individual, comprising the step of topically administering to the individual a therapeutically effective amount of a composition comprising 3D spheroid fibroblasts and a fibroblast-derived material, wherein the fibroblast-derived material is one or more of extracellular vesicles, exosomes, microvesicles, apoptotic bodies, and/or fragments of fibroblast cells.

2. The method of claim 1, further comprising administering to the individual a therapeutically effective amount of one or more of immune cells, keratinocytes, and/or vasal epithelial cells.

3. The method of claim 1, wherein the 3D spheroid fibroblasts comprise myofibroblasts.

4. The method of claim 1, wherein the 3D spheroid fibroblasts are activated, and/or manipulated.

5. The method of claim 3, wherein the 3D spheroid fibroblasts are activated, and/or manipulated, upon exposure to mechanical means and/or exposure to one or more of cytokines, chemokines, growth factors, chemical agents, RNA, micro RNA, RNAi, DNA, viral nucleic acid, and/or exosomes.

6. The method of claim 5, wherein the mechanical means comprises light, laser, pressure, and/or stress.

7. The method of claim 1, wherein the administering is into the wound, adjacent to the wound and/or on the surface of the wound.

8. The method of claim 1, further comprising administering one or more adjuvants to the individual.

9. The method of claim 8, wherein the adjuvant is chemical, mechanical, viral, genetically modified components, or bacterial products-based.

10. The method of claim 1, wherein the individual has diabetes, cancer, or is immunologically compromised.

11. The method of claim 1, wherein the wound is chronic.

12. The method of claim 1, wherein the wound is a cut, abrasion, bedsore, burn, or the individual has more than one of these.

13. The method of claim 1, wherein the individual is administered one or more antibiotics.

14. The method of claim 1, wherein following administration of the composition comprising 3D spheroid fibroblasts to or at the wound, a cover is placed over at least part of the wound.

15. The method of claim 14, wherein the cover acts as a barrier over at least part of the wound to prevent the 3D spheroid fibroblasts to leave the wound.

16. A method of accelerating the healing of one or more wounds in an individual, comprising the step of topically administering to the individual a therapeutically effective amount of a composition comprising 3D spheroid fibroblasts and a fibroblast-derived material, wherein the fibroblast-derived material is one or more of extracellular vesicles, exosomes, microvesicles, apoptotic bodies, and/or fragments of fibroblast cells.

17. The method of claim 16, further comprising administering to the individual a therapeutically effective amount of one or more of immune cells, keratinocytes, and/or vasal epithelial cells.

18. The method of claim 17, wherein said 3D spheroid fibroblasts are activated, and/or manipulated, upon exposure to mechanical means and/or exposure to one or more of cytokines, chemokines, growth factors, chemical agents, RNA, micro RNA, RNAi, DNA, viral nucleic acid, and/or exosomes.

19. The method of claim 18, wherein the mechanical means comprises light, laser, pressure, and/or stress.

* * * * *